US007368576B2

(12) United States Patent
von Hoersten et al.

(10) Patent No.: US 7,368,576 B2
(45) Date of Patent: *May 6, 2008

(54) DIPEPTIDYL PEPTIDASE IV INHIBITORS AND THEIR USES AS ANTI-CANCER AGENTS

(75) Inventors: Stephan von Hoersten, Wedemark (DE); Hans-Ulrich Demuth, Haale (DE); Torsten Hoffmann, Haale (DE)

(73) Assignee: Probiodrug AG, Halle/Salle (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/481,349

(22) Filed: Jul. 5, 2006

(65) Prior Publication Data

US 2006/0293248 A1 Dec. 28, 2006

Related U.S. Application Data

(60) Division of application No. 11/093,991, filed on Mar. 30, 2005, now Pat. No. 7,109,347, which is a continuation of application No. 10/172,809, filed on Jun. 13, 2002, now abandoned.

(60) Provisional application No. 60/301,158, filed on Jun. 27, 2001, provisional application No. 60/360,909, filed on Feb. 28, 2002.

(30) Foreign Application Priority Data

| Jun. 27, 2001 | (EP) | ................................. 01114796 |
| Oct. 12, 2001 | (DE) | ................................. 101 50 203 |
| Nov. 9, 2001  | (DE) | ................................. 101 54 689 |

(51) Int. Cl.
| C07D 277/04 | (2006.01) |
| C07D 277/16 | (2006.01) |
| C07D 277/18 | (2006.01) |
| C07D 291/02 | (2006.01) |
| C07D 291/04 | (2006.01) |

(52) U.S. Cl. ...................................... 548/200; 548/530
(58) Field of Classification Search ..................... None
See application file for complete search history.

(56) References Cited

U.S. PATENT DOCUMENTS

| 2,961,377 A | 11/1960 | Shapiro et al. ............... 167/65 |
| 3,174,901 A | 3/1965 | Sterne et al. .................. 167/65 |
| 3,879,541 A | 4/1975 | Kabbe et al. ................ 424/326 |
| 3,960,949 A | 6/1976 | Ahrens et al. ........... 260/564 B |
| 4,028,402 A | 6/1977 | Fischer et al. .......... 260/501.14 |
| 4,935,493 A | 6/1990 | Bachovchin et al. ........ 530/331 |
| 5,433,955 A | 7/1995 | Bredehorst et al. ......... 424/94.3 |
| 5,462,928 A | 10/1995 | Bachovchin et al. .......... 514/19 |
| 5,512,549 A | 4/1996 | Chen et al. .................... 514/12 |
| 5,543,396 A | 8/1996 | Powers et al. ................ 514/19 |
| 5,552,426 A | 9/1996 | Lunn et al. .................. 514/394 |
| 5,614,379 A | 3/1997 | MacKellar .................. 435/68.1 |
| 5,624,894 A | 4/1997 | Bodor ............................ 514/2 |
| 5,705,483 A | 1/1998 | Galloway et al. .............. 514/12 |
| 5,827,898 A | 10/1998 | Khandwals et al. ......... 514/734 |
| 5,877,202 A * | 3/1999 | Bitonti et al. ................ 514/419 |
| 5,939,560 A * | 8/1999 | Jenkins et al. .............. 548/535 |
| 6,006,753 A | 12/1999 | Efendic ....................... 128/898 |
| 6,011,155 A | 1/2000 | Villhauer ..................... 544/333 |
| 6,107,317 A | 8/2000 | Villhauer ..................... 514/365 |
| 6,110,949 A | 8/2000 | Villhauer ..................... 514/365 |
| 6,124,305 A | 9/2000 | Vollhauer .................... 514/272 |
| 6,172,081 B1 | 1/2001 | Damon ........................ 514/307 |
| 6,201,132 B1 * | 3/2001 | Jenkins et al. .............. 548/535 |
| 6,303,661 B1 | 10/2001 | Demuth et al. .............. 514/866 |
| 6,319,893 B1 | 11/2001 | Demuth et al. ................ 514/2 |
| 6,448,282 B1 | 9/2002 | Phillips et al. .............. 514/400 |
| 6,500,804 B2 | 12/2002 | Demuth et al. ................ 514/19 |
| 6,517,824 B1 | 2/2003 | Kohn et al. .............. 424/78.06 |
| 6,548,481 B1 | 4/2003 | Demuth et al. ................ 514/19 |
| 6,605,589 B1 | 8/2003 | Uckun et al. .................. 514/2 |
| 7,109,347 B2 * | 9/2006 | von Hoersten et al. ..... 548/200 |
| 2001/0025023 A1 | 9/2001 | Carr .............................. 514/2 |

FOREIGN PATENT DOCUMENTS

| DE | 25 42 598 | 4/1976 |
| DE | 296 075 | 11/1991 |
| DE | 196 16 486 | 10/1997 |
| DE | 299 09 210 | 10/1999 |
| DE | 198 26 972 | 12/1999 |

(Continued)

OTHER PUBLICATIONS

Amasheh, et al.; "Electrophysiological analysis of the function of the mammalian renal peptide transporter expressed in *Xenopus laevis* oocytes"; *Journal of Physiology*; (1997); 504(1): 169-174.

Ansorge, et al.; "Membrane-bound peptidases of lymphocytes; Functional implications"; *Biomed. Biochim. Acta*; (1991); 50(4-6); 799-807.

Arai, et al. "Synthesis of Prolyl Endopeptidase Inhibitors and Evaluation of Their Structure-Activity Relationships: In Vitro Inhibition of Prolyl Endopeptidase from Canine Brain"; *Chem. Pharm. Bull.*; (1993); 41(i): 1583-1588.

Ashworth, et al.; "2-Cyanopyrrolidides as Potent, Stable Inhibitors of Dipeptidyl Peptidase IV"; *Bioorganic & Medicinol Chemistry Letters*; (1996); 6(10): 1163-1166.

Augustyns, et al.; "Pyrrolidides: synthesis and structure-activity relationship as inhibitors of dipeptidyl peptidase IV"; *Eur. J. Ed. Chem.*; (1997); 32: 301-309.

(Continued)

*Primary Examiner*—Andrew D. Kosar
(74) *Attorney, Agent, or Firm*—Sonnenschein Nath & Rosenthal LLP

(57) ABSTRACT

The present invention provides new uses of DPIV-inhibitors of the present invention, and their corresponding pharmaceutically acceptable acid addition salt forms, for treating conditions mediated by DPIV or DPIV-like enzymes, such as cancer and tumors. In a more preferred embodiment, the compounds of the present invention are useful for the treatment of metastasis and tumor colonization.

10 Claims, 7 Drawing Sheets

FOREIGN PATENT DOCUMENTS

| | | |
|---|---|---|
| DE | 198 34 610 | 2/2000 |
| EP | 0 658 568 | 6/1995 |
| EP | 0 708 179 | 4/1996 |
| EP | 0 995 440 | 4/2000 |
| EP | 1 130 022 | 9/2001 |
| FR | 2085665 | 12/1971 |
| FR | 2696740 | 4/1994 |
| JP | 04-288098 | 10/1992 |
| JP | 04-334357 | 11/1992 |
| WO | WO 91/11457 | 8/1991 |
| WO | WO 91/16339 | 10/1991 |
| WO | WO 91/17767 | 11/1991 |
| WO | WO 93/01812 | 2/1993 |
| WO | WO 93/08259 | 4/1993 |
| WO | WO 93/20061 | 10/1993 |
| WO | WO 95/11689 | 5/1995 |
| WO | WO 95/15309 | 6/1995 |
| WO | WO 95/22327 | 8/1995 |
| WO | WO 95/29691 | 11/1995 |
| WO | WO 97/40832 | 11/1997 |
| WO | WO 97/45117 | 12/1997 |
| WO | WO 98/19998 | 5/1998 |
| WO | WO 98/22494 | 5/1998 |
| WO | WO 99/41220 | 8/1999 |
| WO | WO 99/41224 | 8/1999 |
| WO | WO 99/46272 | 9/1999 |
| WO | WO 99/61431 | 12/1999 |
| WO | WO 99/62914 | 12/1999 |
| WO | WO 00/01849 | 1/2000 |
| WO | WO 00/10549 | 3/2000 |
| WO | WO 00/53171 | 9/2000 |
| WO | WO 00/53596 | 9/2000 |
| WO | WO 00/58360 | 10/2000 |
| WO | WO 01/09169 | 2/2001 |
| WO | WO 01/32624 | 5/2001 |
| WO | WO 01/34594 | 5/2001 |
| WO | WO 01/62266 | 8/2001 |
| WO | WO 01/74299 | 10/2001 |
| WO | WO 01/89569 | 11/2001 |
| WO | WO 01/94310 | 12/2001 |
| WO | WO 01/97808 | 12/2001 |
| WO | WO 02/13821 | 2/2002 |
| WO | WO 02/20825 | 3/2002 |
| WO | WO 03/016335 | 2/2003 |
| WO | WO 03/070732 | 8/2003 |
| WO | WO 04/089366 | 10/2004 |

OTHER PUBLICATIONS

Badia-Elder, et al; "Effects of Neuropeptide (NPY) on Ethanol Intake and Anxiety in High and Low Alcohol Drinking (Hadi/Ladi) rats"; *Purdue School of Science*; (2000).
Bergmeier; "The Synthesis of Vicinal Amino Alcohols"; *Tetrahedron*; (2000); 56: 2561-2576.
Welch, et al.; "Medical Management of Non-Insulin-Dependent (Type II) Diabetes"; *ADA—Third Edition*; (1994); 3-4.
Campbell, et al.; "Sulphonylureas and metformin: efficacy and inadequacy"; *New Antidiabetic Drugs*; (1990); 33-51.
Chemical Abstract 115; *1-Pharmacology*; (1991); 115: 37.
Chemical Abstract 118; *34-Amino Acids, Peptides, Proteins*; (1993); 118: 933.
Chemical Abstract 126; *7-Enzymes*; (1997); 126(2): 241.
Deacon, et al.; "Both Subcutaneously and Intravenously Administered Glucagon-Like Peptide I are Rapidly Degraded from the $NH_2$-Terminus in Type II Diabetic Patients and in Healthy Subjects"; *Diabetes*; (1995); 4: 1126-1131.
Deacon, et al.; "Degradation of Glucagon-Like Peptide-1 by Human Plasma in Vitro Yields an N-Terminally Truncated Peptide that is a Major Endogenous Metabolite in Vivo"; *J. of Clinical Endocrinology and Metabolism*; (1996); 80: 952-957.
Dodge, et al.; "Folding and Unfolding Kinetics of the Proline-to-Alanine Mutants of Bovine Pancreatic Ribonuclease A'"; *Biochemistry*; (1996); 35: 1548-1559.
Duncan; "Diseases of Metabolism: Detailed Methods of Diagnosis and Treatment"; (1964); 951-957.
Durinx, et al.; "Reference values for plasma dipeptidyl-peptidase IV activity and their association with other laboratory parameters"; *Clin. Chem. Lab. Med.*; (2001); 39(2): 155-159.
Edwards, et al.; "Synthesis and activity of $NH_2$- and COOH-terminal elastase recognition sequences on cotton"; *J. Peptide Res.*; (1999); 54: 536-543.
Endroczi, et al.; "Dipeptidyl Peptidase IV (DP IV) and Superoxide Dismutase Activity in Thymus-Derived Lymphocytes: Effects of Inhibitory Peptides and $ZN^{2=}$ In Vitro"; *Acta Physiologica Hungarian* (1996); 75(1): 35-44.
Frohman, et al.; "Rapid Enzymatic Degradation of Growth Hormone-releasing Hormone by Plasma In Vitro and In Vivo to a biologically Inactive Product Cleaved at the $NH_2$ Terminus"; *J. Clin. Invest.*; (1986); 78: 906-913.
Gomez, et al.; "Relationship between endo- and expopetidases in a processing enzyme system: Activation of an endoprotease by the aminopeptidase B-like activity in somatostatin-28 convertase"; *Proc. Natl. Acad. Sci. USA*; (1988); 85: 5468-5472.
Goodman & Gilman's; "Hormone and Hormone Antagonists"; *The Pharmacological Basis of Therapeutics Ninth Edition*; (1996); 1510.
Gossrau; "Cytochemistry of membrane proteases"; *Histochem J.*; (1985) 17(7): 737-71
Gutniak, et al.; "Antidiabetogenic Effect of Glucagon-Like Peptide-1 (7-36) Amide in Normal Subjects and Patients with Diabetes Mellitus"; *New England J. Med.*; (1992); 326: 1316-1322.
Gutniak, et al.; "Subcutaneous Injection of the Incretin Hormone Glucagon-Like Peptide 1 Abolishes Postprandial Glycemia in NIDDM"; *Diabetes Care*; (1994); 17(9): 1039-1044.
Hahn, et al.; "Enzyme histochemical evidence for the presence of potential blood pressure regulating proteases in cultured villous explants from human first trimester placentae"; *Acta Histochem*; (1993); 95(2): 185-92.
Demuth; "Recent Developments in Inhibiting cysteine and Serine Proteases"; *J. Enzyme Inhibition*; (1990); 3: 249-278.
Hegen, et al.; "The T Cell Triggering Molecule Tp103 is Associated with Dipeptidyl Aminopeptidase IV Activity"; *The Journal of Immunology*; (1990); 144(8): 2908-2914.
Hendrick, et al.; "Glucagon-like Peptide-1-(7-37) Suppresses Hyperglycemia in Rats"; *Metabolism Clinical and Experimental*; (1993); 42(1): 1-6.
Heymann & Mentlein; "Has dipeptidyl peptidase IV an effect on blood pressure and coagulation"; *Klin Wochenschr*; (1984); 62(1): 2-10.
Krausslich & Wimmer; "Viral Proteinases"; *Ann. Rev. Biochem.*; (1988); 57: 701-754.
Hoffmann, et al.; "Inhibition of dipeptidyl peptidase IV (DP IV) by anti-DP IV antibodies and non-substrate X-X-Pro- oligopeptides ascertained by capillary electrophoresis"; *Journal of Chromatography A*; (1995); 716: 355-362.
Holst & Deacon; "Perspectives in Diabetes: Inhibition of the Activity of Dipeptidyl-Peptidase IV as a Treatment for Type 2 Diabetes"; *Diabetes*; (1998); 47(11): 1663-1670.
Lee & Lee; "Cathepsin B inhibitory peptides derived from •-casein"; *Peptides*; (2000); 21: 807-809.
Index Nominum—International Drug Directory 92/93.
Ishiura, et al.; "Identification of a putative amyloid A4-generating enzyme as a prolyl endopeptidase"; *National Institute of Neuroscience*; (1990); 260(1): 131-134.
Kawamoto & Wills; "Enantioselective synthesis of •-hydroxy amines and aziridines using asymmetric transfer hydrogenation of •-amido ketones"; *Tetrahedron: Asymmetry*; (2000); 11: 3257-3261.
Kessler; "Konformation and biologische Wirkung von cyclischen Peptiden"; *Angew Chem.*; (1982); 94: 509-520.
Kieffer, et al.; "Degradation of Glucose-Dependent Insulinotropic Polypeptide and Truncated Glucagon-Like Peptide 1 in Vitro and in Vivo by Dipeptidyl Peptidase IV"; *Endocrinology*; (1995); 136: 3585-3596.

Kirschke, et al.; "Proteinases 1: lysosomal cysteine proteinases"; *Protein Profile*; (1995); 2: 1587-1634.

Korom, et al.; "Inhibition of CD26/Dipeptidyl Peptidase IV Activity in Vivo Prolongs Cardiac Allograft Survival in Rat Recipients"; *Transplantation*; (1997); 54(10): 1495-1500.

Lader; "Assessment Methods and the Differential Diagnosis of Anxiety"; *Journal of Clinical Psychopharmacology*; (1981); 1(6): 342-349.

Lin, et al.; "Inhibition of dipeptidyl peptidase IV by fluoroolefin-containing N-peptidyl-O-hydroxylamine peptidomimetics"; *Proc. Nat. Acad. Sci. USA*; (1998); 95: 14020-14024.

Magyar, et al.; "Proximal rubule Na transporter responses are the same during acute and chronic hypertension"; *Am. J. Physiol. Renal. Physiol.*; (2000); 279(2) F358-369.

Mannucci, et al.; "Effect of Metformin on Glucagon-Like Peptide 1 (GLP-1) and Leptin Levels in Obese Nondiabetic Subjects"; *Diabetes Care*; (2001); 24(3): 489-494.

Martindale: The Extra Pharmacopoeia—Thirtieth Edition (1993) p. 1619.

Martindale: The Extra Pharmacopoeia—Thirtieth Edition (1993) p. 36.

Mentlein, et al.; "Proteolytic processing of neuropeptide Y and peptide YY by dipeptidyl peptidase IV"; *Regulatory Peptides*; (1993); 49: 133-144.

Mentlein, et al.; "Dipeptidyl-peptidase IV hydrolyses gastric inhibitory polypeptide, glucagon-like peptide-1(7-36)amide, peptide histidine methionine and is responsible for their degradation in human serum"; *Eur. J. Biochem.*; (1993); 214: 829-835.

Munglani, et al.; "The Therapeutic Potential of Neuropeptide Y"; *Review Article Cambridge University*; (1996); 371-389.

Nathan, et al.; "Insulinotropic Action of Glucagonlike Peptide-1-(7-37) in Diabetic and Nondiabetic Subjects"; *Diabetes Care*; (1991); 15(2): 270-276.

Nauck, et al.; "Normalization of fasting hyperglycaemia by exogenous glucagon-like peptide 1(7-36 amide) in Type 2 (non-insulin-dependent) diabetic patients"; *Diabetologia*; (1993); 741-744.

Orakov, et al.; "Proglucagon Products in Plasma of Noninsulin-dependent Diabetics and Nondiabetic Controls in the Fasting State and after Oral Glucose and Intravenous Arginine"; *J. Clin. Invest.*; (1991); 87: 415-423.

Papies, et al.; "Isoenzyme (lactate dehydrogenase, aspartate aminotransferase) and dipeptidyl peptidase IV activity changes in blood plasma likely indicative of organ involvement due to arterial hypertension"; *Cor Vasa*; (1991); 33(3): 218-26.

Pauly, et al.; "Improved Glucose Tolerance in Rats Treated with the Dipeptidyl Peptidase IV (CD26) Inhibitor Ile-Thiazolidide"; *Metabolism*; (1999); 48(3) 385-389.

Pauly, et al.; "Abstracts Issue: Abstracts from the 11th International Symposium on Regulatory Peptides"; *Regulatory Peptides*; (1996); 64(103): 148.

Pederson, et al.; "Improved glucose tolerance in Zucker fatty rats by oral administration of the dipeptidyl peptidase IV inhibitor isoleucine thiazolidide"; *Diabetes*; (1998); 47(8): 1253(6).

Psychyrembel Klinisches Worterbuch (1993).

Qureshi, et al.; "Endogenous neuropeptide Y mediates vasoconstriction during endotoxic and hemorrhagic shock"; *Regul. Pept.*; (1998) 75-76: 215-20.

Reinhold, et al.; "Inhibitors of dipeptidyl peptidase IV/CD26 suppress activation of human MBP-specific CD4 = T cell clones"; *Journal of Neuroimmunology*; (1998); 87: 203-209.

Sengupta, et al.; "Amino Acid Derived Morpholine Amides for Nucleophilic •-Amino Acylation Reactions: A New Synthetic Route to Enantiopure •-Amino Ketones"; *Tetrahedron Letters* (1999); 40:4107-4110.

Smith, et al.; "Disease and Disorders of Metabolism: Deficiency Diseases—Diabetes Mellitus"; *Veterinary Pathology*; (1972); 1018-1020.

Snow and Bachovchin; "Boronic Acid Inhibitors of Dipeptidyl Peptidase IV: A New Class of Immunosuppressive Agents"; *Advances in Medicinal Chemistry*; (1995); 3: 149-177.

Stockel-Maschek, et al.; "Thioxo amino acid pyrrolidides and thiazolidides: new inhibitors of proline specific peptidases"; *Ciochimica et Biophysica Acta* (2000); 1479: 15-31.

Stryer; "Amino Acid Degradation and the Urea Cycle: Garrod's Discovery of Inborn Errors of Metabolism"; *Biochemistry*; (1975); 451-452.

Stryer; "Protein Conformation, Dynamics and Function"; *Biochemistry—Third Edition*; (1975); 191-193.

Tanaka, et al.; "Suppression of Arthritis by the Inhibitors of Dipeptidyl Peptidase IV"; *Int. J. Immunopharma*; (1997); 19(1) 15-24.

The Merck Index—Eleventh Edition; (1989); 934.

The Merck Index—Ninth Edition; (1976); 773.

The Merck Index—Twelfth Edition; (1996); 1014.

Thorens and Waeber; "Glucagon-Like Peptide-1 and the Control of Insulin Secretion in the Normal State and in NIDDM"; *Diabetes*; (1993); 42: 1219-1225.

Vallee and Martel; "Larval development of *Tribolium confusum* in the presence of non-naturally occurring amino acide"; *Annales de l'ACFAS*; (1962); 28: 26-27.

Gault, et al.; "Glucose-dependent insultinotropic polypeptide analogues and their therapeutic potential for the treatment of obesity-diabetes"; *BBRC*; (2003); 308: 207-213.

Vidal (1993) "Gluconate de Calcium Lavoisier".

Wakselman, et al.; "Inhibition of HIV-1 Infection of CD26⁻but not CD26 Cells by a Potent Cyclopeptidic Inhibitor of the DPP IV Activity of CD26"; *J. Med. Chem.*; (1993); 36: 1539.

Walter, et al.; "Proline Specific Endo-and Exopeptidases"; *Molecular & Cellular Biochemistry*; (1980); 30(2): 111-127.

Wetzel, et al.; "Effects of the CLIP fragment ACTH 20-24 on the duration of REM sleep episodes"; *Neuropeptides*; (1997); 31(1): 41-45.

Willms; et al; "Gastric Emptying, Glucose Responses, and Insulin Secretion after a Liquid Test Meal: Effects of Exogenous Glucagon-Like Peptide-1 (GLP-1)-(7-36) Amide in Type 2 (Noninsulin-Dependent) Diabetic Patients"; *J. of Clinical Endocrinology and Metabolism*; (1996); 81(1): 327-332.

Winslow; "Novartis Drug Alters Picture for Diabetes"; *The Wall Street Journal*; (2000); p. B2.

Yaron and Naider; "Proline-Dependent Structural and Biological Properties of Peptides and Proteins"; *Critical Reviews in Biochemistry and Molecular Biology*; (1993); 28(1): 31-81.

Chen and Kelly; "Seprase Complexes in Cellular Invasiveness"; *Cancer and Metastasis Review*; (2003); 22: 259-269.

Wettstein, et al.; "Central Nervous System Pharmacology of Neuropeptide Y"; *Pharmac. Ther.*; (1995); 65: 397-414.

Vanhoof, et al. "Proline and Peptide Conformation"; *The FASEB Journal:* (1995); 9: 736-744.

Shaw, et al.; "Cystein and Serine Protease Inhibitors Block Intracellular Development and Disrupt the Secretory Pathway of *Toxoplasma gondii*"; *Microbes and Infection*; (2002); 4: 119-132.

Bromme and Kurschke; "N-Peptidyl-O-Carbamoyl Amino Acid Hydroxamates: Irreversible inhibitors for the Study of the S2 Specificity of Cysteine Proteinases"; *FEBS*; (1993); 322(3): 211-214.

Brachwitz; "Hydroximino Acid Derivatives. IV. 3-Acyl-1,2,4-Oxadiazoles From N-Acyl and N-Ethoxycarbonyl-Alpha-Amino Ketones". *CAPLUS*; (1972); 76: 113134.

Gault, et al.; "Characterization of the Cellular and Metabolic Effects of a Novel Enzyme-Resistant Antagonist of a Glucose-Dependent Insulinotropic Polypeptide"; *Biochemical and Biophysical Research Communications*; (2002); 290: 1420-1426.

Hinke, et al.; "Dipeptidyl Peptidase IV-Resistant [D-Ala$^2$]Glucose-Dependent Insulinotropic Polypeptide (GIP) Improves Glucose Tolerance in Normal and Obese Diabetic Rats"; *Diabetes*; (2002); 51: 652-661.

Hinke, et al.; Identification of a bioactive domain in the amino-terminus of glucose-dependent insulinotropic polypeptide (GIP); *Biochimica et Biophysica Acta*; (2001); 1547: 143-155.

Kuhn-Wache, et al.; "Analogs of Glucose-Dependent Insulinotropic Polypeptide with Increased Dipeptidyl Peptidase IV Resistance"; *Cellular Peptidase in Immune Functions and Diseases 2*; (2000); 187-195.

Schilling, et al.; "Glutaminyl cyclases unfold glutamyl cyclase activity under mild acid conditions"; *FEBS Letters*; (2004); 563: 191-196.

Misquitta, et al.; "Inhibition Studies of Glutaminyl Cyclase"; *FASEB Journal*; (2001); 15(5): A1159.

Misquitta, et al.; "Characterization of the Inhibitionof Glutaminyl cyclase by Imidazole Derivatives and Phenanthrolines"; *FASEB Journal*; (2002); 16(4): A157.

Ganellin, et al.; "Design of Potent Non-Thiourea $H_3$-Receptor Histamine Antagonists"; *J. Med. Chem.*; (1995); 38: 3342-3350.

Liu, et al.; "Nonpeptide Somatostatin Agonists with $sst_4$, Selectivity: Synthesis and Structure-Activity Relationships of Thioureas"; *J. Med. Chem.*; (1998); 41: 4693-4705.

Wright, et al.; "Thromboxane Synthetase Inhibitors and Antihypertensive Agents. 4. N-[(1H-Imidazol-1-yl)alkyl] Derivatives of Quinazoline-2,4(1H,3H)-diones, Quinazolin-4(3H)-ones, and 1,2,3-Benzotriazin-4(3H)-ones"; *J. Med. Chem.*; (1987); 30: 2277-2283.

Clader, et al.; "Substituted (1,2-Diarylethyl)amide Acyl-CoA:Cholesterol Acyltransferase Inhibitors: Effect of Polar Groups on in Vitro and in Vivo Activity"; *J. Med. Chem.*; (1995); 38: 1600-1607.

Venkatachalam, et al.; "Anti-HIV Activity of Aromatic and Heterocyclic Thiazolyl Thiourea Compounds"; *Bioorganic & Medicinal Chemistry Letters*; (2001); 11: 523-528.

Moon, et al.; "Cholinergic Activity of Acetylenic Imidazoles and Related Compounds"; *J. Med. Chem.*; (1991); 34: 2314-2327.

Wright, et al.; "Thromboxane Synthetase Inhibitors and Antihypertensive Agents. 1. N-[(1H-Imidazol-1-yl)alkyl]aryl Amides and N-[(1H-1,2,4-Triazol-1-yl)alkyl]aryl Amides"; *J. Med. Chem.*; (1986); 29: 523-530.

Hinke, et al.; "Further Development of Antidiabetic Enzyme Resistant Incretin Analogues"; *Diabetologia*; (2002); pp. 176-177.

\* cited by examiner

DIPEPTIDYL PEPTIDASE IV INHIBITORS AND THEIR USES AS ANTI-CANCER AGENTS

RELATED APPLICATIONS

This application is a Divisional application of U.S. application Ser. No. 11/093,991 entitled Dipeptidyl Peptidase IV Inhibitors and Their Uses as Anti-Cancer Agents filed on Mar. 30, 2005, now U.S. Pat. No. 7,109,347 which is a Continuation of 10/172,809 entitled Dipeptidyl Peptidase IV Inhibitors and Their Uses as Anti-Cancer Agents filed on Jun. 13, 2002, now abandoned which claims the priority of US provisional application US 60/301,158 entitled Peptide Structures Useful for Competitive modulation of Dipeptidyl Peptidase IV Catalysis filed on Jun. 27, 2001. Priority is also claimed from U.S. provisional application US 60/360,909 entitled Glutaminyl-based DPIV Inhibitors filed on Feb. 28, 2002. This application also claims the priority of the following foreign applications EP 01 114 796.4 entitled Peptide Structures Useful for Competitive Modulation of Dipeptidyl Peptidase IV Catalysis having a priority date of Jun. 27, 2001, DE 101 50 203.6 entitled Peptidylketone als Inhibitoren der DPIV having a priority date of Oct. 12, 2001 and DE 101 54 689.0 entitled Substituierte Aminoketonverbindungen having a priority date of Nov. 9, 2001. The above applications are incorporated in their entirety by reference.

FIELD OF THE INVENTION

The present invention relates to inhibitors of dipeptidyl peptidase IV and dipeptidyl peptidase IV-like enzyme activity and, more particularly, pharmaceutical compositions containing said compounds, and the use of said compounds for the treatment of cancer and tumors. The present invention especially provides a method for the inhibition of metastasis and tumor colonization.

BACKGROUND ART

Dipeptidyl peptidase IV (DPIV) is a serine protease which cleaves N-terminal dipeptides from a peptide chain containing, preferably, a proline residue in the penultimate position. Although the biological role of DPIV in mammalian systems has not been completely established, it is believed to play an important role in neuropeptide metabolism, T-cell activation, attachment of cancer cells to the endothelium and the entry of HIV into lymphoid cells.

Likewise, it has been discovered that DPIV is responsible for inactivating glucagon-like peptide-1 (GLP-1) and glucose-dependent insulinotropic peptide also known as gastric-inhibitory peptide (GIP). Since GLP-1 is a major stimulator of pancreatic insulin secretion and has direct beneficial effects on glucose disposal, in WO 97/40832 and U.S. Pat. No. 6,303,661 inhibition of DPIV and DPIV-like enzyme activity was shown to represent an attractive approach for treating non-insulin-dependent diabetes mellitus (NIDDM).

The present invention provides a new use of DPIV-inhibitors for the treatment of conditions mediated by inhibition of DPIV and DPIV-like enzymes, in particular the treatment of cancer and tumors and the inhibition of metastasis and tumor colonization, and pharmaceutical compositions e.g. useful in inhibiting DPIV and DPIV-like enzymes and a method of inhibiting said enzyme activity.

This invention relates to a method of treatment, in particular to a method for the treatment of cancer, tumors, metastasis and tumor colonization and to compositions for use in such method. Dipeptidyl peptidase IV (DPIV) is a post-proline (to a lesser extent post-alanine, post-serine or post-glycine) cleaving serine protease found in various tissues of the body including kidney, liver, and intestine.

It is known that DPIV-Inhibitors may be useful for the treatment of impaired glucose tolerance and diabetes mellitus (International Patent Application, Publication Number WO 99/61431, Pederson R A et al, Diabetes. 1998 August; 47(8):1253-8 and Pauly R P et al, Metabolism 1999 March; 48(3):385-9). In particular WO 99/61431 discloses DPIV-Inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples of low molecular weight dipeptidyl peptidase IV inhibitors are agents such as tetrahydroisoquinolin-3-carboxamide derivatives, N-substituted 2-cyanopyroles and -pyrrolidines, N—(N'-substituted glycyl)-2-cyanopyrrolidines, N-(substituted glycyl)-thiazolidines, N-(substituted glycyl)-4-cyanothiazolidines, amino-acyl-borono-prolyl-inhibitors, cyclopropyl-fused pyrrolidines and heterocyclic compounds. Inhibitors of dipeptidyl peptidase IV are described in U.S. Pat. No. 6,380,398, U.S. Pat. No. 6,011,155; U.S. Pat. No. 6,107,317; U.S. Pat. No. 6,110,949; U.S. Pat. No. 6,124,305; U.S. Pat. No. 6,172,081; WO 95/15309, WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, the teachings of which are herein incorporated by reference in their entirety.

The term DPIV-like enzymes relates to structurally and/or functionally DPIV/CD26-related enzyme proteins (Sedo & Malik, Dipeptidyl peptidase IV-like molecules: homologous proteins or homologous activities? Biochimica et Biophysica Acta 2001, 36506: 1-10). In essence, this small group of enzymes has evolved during evolution to release H-Xaa-Pro-Dipeptides and H-Xaa-Ala-Dipeptides from N-terminus of oligo- or polypeptides. They show the common feature, that they accomotate in the Pro-position also Al, Ser, Thr and other amino acids with small hydrophobic side-chains as, Gly or Val. The hydrolytic efficacy is ranked Pro>Ala>>Ser, Thr>>Gly, Val. Same proteins have been only available in such small quantities, that only the post-Pro or post-Ala cleavage could be established. While the proteins: DPIV, DP II, FAPα (Seprase), DP 6, DP 8 and DP 9 are structurally related and show a high sequence homology, attractin is an extraordinary functional DPIV-like enzyme, characterized by a similar activity and inhibitory pattern.

Further DPIV-like enzymes are disclosed in WO 01/19866, WO 02/04610, WO 02/34900 and WO02/31134. WO 01/19866 discloses novel human dipeptidyl aminopeptidase (DPP8) with structural und functional similarities to DPIV and fibroblast activation protein (FAP). WO 02/04610 provides reagents, which regulate human dipeptidyl peptidase IV-like enzyme and reagents which bind to human dipeptidyl peptidase IV-like enzyme gene product. These reagents can play a role in preventing, ameliorating, or correcting dysfunctions or diseases including, but not limited to, tumors and peripheral and central nervous system disorders including pain and neurodegenerative disorders. The dipeptidyl peptidase IV-like enzyme of WO 02/04610 is well known in the art. In the Gene Bank data base, this enzyme is registered as KIAA1492 (registration in February 2001, submitted on Apr. 4, 2000, AB040925). In the Merops data base, the dipeptidyl peptidase IV-like enzyme of WO 02/04610 is registered as non-protease homologue, because the active site serine motive is GKGYGG in contrast to DPIV, which has a active site serine motive consisting of GWSYGG. The Merops homologue of the dipeptidyl peptidase IV-like enzyme disclosed in WO 02/04610 and the active site motive thereof was confirmed by the human genome project. WO 02/34900 discloses a novel dipeptidyl peptidase 9 (DPP9) with significant homology with the amino acid sequences of DPIV and DPP8. WO 02/31134 discloses three DPIV-like enzymes, DPRP1, DPRP2 and DPRP3. Sequence analysis revealed, that DPRP1 is identical to DPP8, as disclosed in WO 01/19866, that DPRP2 is identical to DPP9 and that DPRP3 is identical to KIAA1492 as disclosed in WO 02/04610.

DPIV and DPIV-Like Enzymes in Immunophysiology and Cancer

Dipeptidyl peptidase IV (DPIV; EC 3.4.14.5; CD26) CD26 is a M r 110,000 surface glycoprotein with an array of diverse functional properties that is expressed on a number of tissues, including epithelial cells and leukocyte subsets (Mentlein, 1999). Furthermore, it is a membrane-associated ectopeptidase that possesses DPIV-like activity in its extracellular domain and is able to cleave N-terminal dipeptides from polypeptides with either L-proline or L-alanine in the penultimate position. In general, DPIV is recognized as an ectopeptidase with a triple functional role. DPIV is involved in catalyzing the release of Xaa-Pro dipeptides from circulating hormones and chemokines (De Meester et al, 1999; Mentlein, 1999), in T cell dependent immune responses (Kähne et al, 1999; Korom et al, 1997), and in cell adhesion including metastasis (Mentlein, 1999).

In addition DPIV has been identified as the ADA binding protein, thereby regulating ADA surface expression, with the DPIV/ADA complex perhaps playing a key role in the catalytic removal of local adenosine to regulate immune system function. Besides being a key immunoregulatory molecule, DPIV may have a potential role in the development of certain neoplasms (Mattern et al., 1993; Carbone et al., 1995). In eukaryotic cells, cell cycle progression is controlled at the G1-S checkpoint by a group of related enzymes known as the CDKs, which are positively regulated by their physical association with regulatory subunits called cyclins. It has been demonstrated that binding of soluble anti-CD26 antibodies inhibits the growth of anaplastic large cell T-cell lymphoma cell lines, both in in vitro and in vivo experiments (Ho et al., 2001).

Cancer Pathomechanisms

Cancer is a group of over 150 diseases characterized by the uncontrolled growth of abnormal cells in the body. Normal cells can become abnormal when they are exposed to carcinogens such as radiation or particular drugs or chemicals. They can also turn malignant (cancerous) when they are attacked by certain viruses or when some not-yet-fully-understood internal signal occurs. Once cells become malignant, they multiply more rapidly than usual. Then they often form masses called tumors that invade nearby tissue and interfere with normal bodily functions. Cancer cells also have a tendency to spread to other parts of the body, where they may form a secondary tumor.

Mechanisms of Metastasis

The outcome of cancer metastasis depends on multiple interactions within the target tissue and depends on the microenvironment including cellular adhesion molecules (Carlos, 2001), chemokines (Muller et al., 2001), or hydrodynamic effects (Haier and Nicholson, 2001) and many other factors (Fidler, 2001). In addition, a very rapid attraction of leukocytes and specific cellular responses at the tumor sites may play a critical role in the early host defense against cancer (Shingu et al.; 2002). These early changes may be of critical importance for the outcome of metastatic disease and may extend the present understanding of the host resistance against metastasis.

DPIV and DPIV-Like Enzymes and Tumor Adhesion and Colonization

For cancer cell or metastatic cell adhesion, a prominent expression of DPIV on endothelia of lung capillaries accounts for arrest of blood borne breast cancer cells (Johnson et al, 1993). Fibronectin (FN) and probably also collagen collected on the breast cancer cell surface were identified as the principal ligands for DPIV (Abdel-Ghany et al, 1998; Cheng et al, 1998).

Ho and colleagues (2001) show that binding of soluble anti-CD26 monoclonal Ab 1F7 inhibits the growth of the human CD301 anaplastic large cell T-cell lymphoma cell line Karpas 299 in both in in vitro and in vivo experiments. In vitro experiments show that 1F7 induces cell cycle arrest at the G1-S checkpoint, associated with enhanced p21 expression that is dependent on de novo protein synthesis. Furthermore, experiments with a severe combined immunodeficient mouse tumor model demonstrate that 1F7 treatment significantly enhances survival of tumor-bearing mice by inhibiting tumor formation.

Protease Inhibitors, Antibodies and Proteases as Anti-Tumor Agents

WO 95/29691 discloses proline phosphonate derivatives as inhibitors of serine proteases with chymotrypsin-like, trypsin-like, elastase-like and dipeptidyl peptidase IV specificity and their roles as anti-inflammatory agents, anticoagulants, anti-tumor agents and anti-AIDS agents.

WO 98/53812 and WO 97/48409 disclose novel methods of using phosphonate derivatives, hydroxyphosphinyl derivatives, and phosphoramidate derivatives to inhibit N-Acetlyated α-Linked Acidic Dipeptidase (NAALADase) enzyme activity, and to treat prostate diseases, especially using these compounds for the inhibition of prostate cancer cell growth.

WO 01/92273 discloses new benzenedicarboxylic acid derivative compounds, pharmaceutical compositions, diagnostic methods and diagnostic kits that include those compounds and methods of using those compounds for inhibiting NAALADase enzyme activity, detecting diseases where NAALADase levels are altered, affecting neuronal activity, affecting TGF-β activity, inhibiting angiogenesis and treating glutamate abnormalities, neuropathy, pain, compulsive disorders, prostate diseases, cancer and glaucoma.

WO 01/34596 discloses pyrrolecarbonylimino derivatives, pharmaceutical compounds and methods of using those compounds to inhibit NAALADase enzyme activity, thereby affecting neuronal activities, inhibiting angiogenesis and treating glutamate abnormalities, compulsive disorders, prostate diseases and cancer.

WO 00/71135 discloses a method for treating subjects with abnormal cell proliferation. The method involves administering to subjects in need of such treatment an effective amount of boro-proline compounds, to inhibit cell proliferation such as that associated with tumor growth and metastasis. A method for inhibiting angiogenesis in an abnormal proliferative cell mass by the administration of a boro-proline derivative is also provided. The invention of WO 00/71135 is based, in part, on the observation, that the boro-proline derivatives are able to inhibit the enzymatic activity of fibroblast activation protein-alpha (FAP-α).

WO 00/71571 relates to a prodrug that is capable of being converted into a drug by the catalytic action of human fibroblast activation protein-alpha (FAP-α), said prodrug having a cleavage site which is recognised by FAP-α, and said drug being cytotoxic or cytostatic under physiological conditions. These prodrugs are converted into a drug at the site of the tumor.

WO 00/10549 discloses compounds and a method for regulation of substrate activity in vivo useful for the treatment of medical disorders such as arteriosclerosis, allergies, inflammation, angiogenesis, cardiogenesis, neoplasm, tumor, cancer, a hepatic disease, an intestinal disease, organ vascularization, and microbial and viral infections. The compounds consist of a targeting moiety that binds to DPIV, and a reactive group, that reacts at a reactive center of DPIV. Said compounds are used to prevent chemokine alteration by inhibiting DPIV activity.

WO 00/36420 discloses a method for identifying nucleotide sequences that are differentially expressed in tumor cells, preferably primary breast tumor cells, comprising exposing a tumor cell containing tissue sample to an agent specific for fibroblast activation protein (FAP) separating cells recognised by said agent from the remaining cells in the sample and harvesting said remaining cells. Nucleic acid molecules derived from the use of this technique are also described, together with compositions comprising the same and their uses in pharmaceutical compositions for treating a disease, preferably breast cancer.

WO 99/47152 discloses a method of suppressing the malignant phenotype or inducing apoptosis of cancer cells in a subject, comprising introducing into the cancer cell an amount of a nucleic acid encoding a dipeptidyl peptidase IV protein or fibroblast activating protein-α, thereby suppressing the malignant phenotype of the cancer. WO 99/47152 also discloses a method of inducing expression of dipeptidyl peptidase IV or fibroblast activating protein-α in cancer cells of a subject, comprising administering to the subject a pharmaceutical composition comprising a therapeutically effective amount of an agent capable of activating transcription of the dipeptidyl peptidase IV gene or fibroblast activating protein-α gene and a pharmaceutical acceptable carrier or diluent.

WO 01/74299 discloses antibodies that specifically bind to a membrane protease complex, the complex consisting of two homodimers of seprase and dipeptidyl peptidase IV (DPIV), obtained from mammalian, preferably human cell membranes. The antibodies specifically bind to the DPIV protease of the seprase-DPIV complex. This membrane protease complex resides on cell surface invadopodia at the leading edge of angiogenic endothelia, migratory fibroblasts, and invading cancer cells.

WO 02/20825 relates to novel methods and compositions for detection and isolation of cancer cells with metastatic potential. WO 02/20825 further relates to assays for measuring the metastatic potential of such cancer cells and drug screening assays for the indentification of agents having anti-metastatic potential. Also disclosed are methods and compositions for inhibiting the metastatic potential of cancer cells by modulating the activity of serine integral membrane proteases [(SIMP) consisting of seprase and dipeptidyl peptidase IV (DPIV)] expressed on the surface of metastasizing cancer cells, by using antibodies against SIMP.

Current Treatments of Cancer and Tumor Cell Adhesion

Current cancer treatment regimens comprise surgery, chemotherapy, radiation therapy, and other treatment methods including immunotherapy. Immunotherapy is composed of the usage or the modification of intrinsic bodily mechanisms—in most cases immune mechanisms—to fight cancer. Chemotherapy kills cancer cells through the use of drugs or hormones. Taken either orally or through injection, chemotherapeutic agents are used to treat a wide variety of cancer. They may be given alone or in combination with surgery or radiation or both. Chemotherapy is an established way to destroy hard-to-detect cancer cells that have spread and are circulating in the body. Anemia (low number of red blood cells) is a frequent side effect of chemotherapy and may cause symptoms such as extreme tiredness, dizziness, or shortness of breath. Epoetin alfa (Procrit®, Epogen®)—recombinant erythropoietin that stimulates red blood cell production—is a prescription drug available for the treatment of chemotherapy-related anemia.

Immunotherapy uses the body's own immune system or other parts of the organism to destroy cancer cells. This form of treatment is still being intensively studied in clinical trials; it is not yet widely available to most cancer patients. The various immunological agents used include substances produced by the body (such as the interferons, the interleukins and tumor necrosis factor) and laboratory-produced substances (such as monoclonal antibodies and vaccines). Immunological agents work in different ways and can be used independently or in combination with other forms of treatment.

Angiogenesis Inhibitors as Anti-Metastatic Drugs in Immunotherapy

Angiogenesis inhibitors are drugs that block the development of new blood vessels. Solid tumors cannot grow without inducing the formation of new blood vessels. Blocking the development of new blood vessels cuts off the tumor's supply of oxygen and nutrients.

Several angiogenesis inhibitors are currently being tested in human trials. In cancerous tissue, tumors cannot grow or spread (metastasize) without the development of new blood vessels. Blood vessels supply tissues with oxygen and nutrients necessary for survival and growth.

SUMMARY OF THE INVENTION

The present invention provides new uses of DPIV-inhibitors of formulas 1 to 12, and their corresponding pharmaceutically acceptable acid addition salt forms for treating cancer and tumors. In a more preferred embodiment, the compounds of the present invention are useful for the prevention and inhibition of metastasis and tumor colonization.

Reduced expression of the ectopeptidase DPIV and lack of DPIV-like activity in lungs of mutant F344 rats lacking DPIV enzymatic activity and expression results in reduced adhesion of cancer cells and in reduced lung metastasis. In vivo cell adhesion and growth of the F344 rat syngeneic mammary adenocarcinoma MADB106 was studied in F344 rats after acutel and chronic treatment with DPIV-ligands in vivo. Mutant F344 substrains lacking DPIV enzymatic activity and wild-type-like F344 were tested. Chronic intragastric infusion of isoleucyl cyano pyrrolidine TFA and isoleucyl thiazolidine fumarate via osmotic minipumps over two weeks dose-dependently reduced the cancer-induced weight loss and the number of tumor colonies on the lung surface. Thus, metastasis of MADB106 is reduced by chronic treatment using different DPIV Inhibitors (isoleucyl thiazolidine fumarate; isoleucyl cyano pyrrolidine TFA) suggesting protective-like class effects by the two different DPIV-inhibitior/ligands. Possibly, isoleucyl thiazolidine fumarate and isoleucyl cyano pyrrolidine TFA protect from metastasis either via interaction with cell adhesion processes, via a modification of the cellular host defense mechanisms, via modulation of angiogenesis, via direct effects on cancer cells, or via increased levels of DPIV substrates, which indirectly mediate protective-like effects.

DETAILED DESCRIPTION OF THE INVENTION

Figure 1:
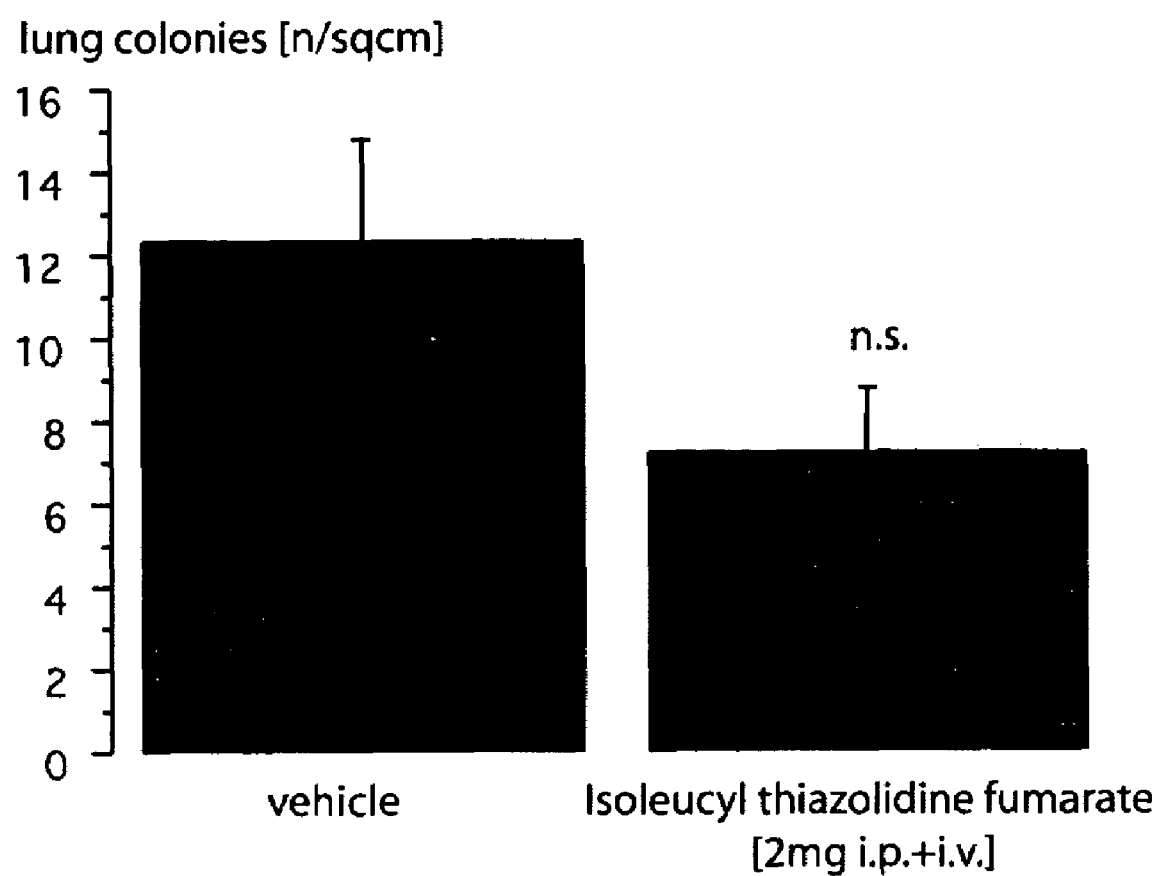
FIG. 1: Effect of single injection of isoleucyl thiazolidine fumarate on lung metastasis in F344 rats. Vital dye (Carboxyfluorescein; CFSE) labeled MADB106 tumor cells were injected via the lateral tail vein and lungs were collected 30 min after inoculation. CFSE positive tumor cells in lungs were quantified by means of immunohistology and image analysis. Data represent means±SEM; no significant differences vs. saline treated controls were found.

The present invention relates to the area of dipeptidyl peptidase IV (DPIV) inhibition and, more particularly, to a new use of inhibitors of DPIV and DPIV-like enzyme activity for the treatment of cancer and tumors, in particular for the prevention and inhibition of metastasis and tumor colonization, and pharmaceutical compositions containing said compounds.

In contrast to other proposed methods in the art, the present invention provides an orally available therapy with low molecular weight inhibitors of dipeptidyl peptidase IV. The instant invention represents a novel approach for the treatment of cancer and metastatic disease. It is user friendly, commercially useful and suitable for use in a therapeutic regime, especially concerning human diseases.

Spontaneous mutations of the DPIV gene observed in substrains of F344 rats provide a model for studying the role of DPIV in tumor adhesion and colonization. The mutations in F344 rats result in a lack of DPIV enzymatic activity and are found in substrains from Germany (GER) and Japan (JAP) (Thompson et al, 1991; Tsuji et al, 1992), while rats from USA breeders show significant enzyme activity. In F344JAP rats, a G633R substitution in the DPIV protein causes markedly reduced expression of a mutant inactive enzyme (Cheng et al, 1999; Tsuji et al, 1992;), while the other DPIV negative F344GER substrain expresses a non-active mutant enzyme (Thompson et al, 1991). Studies by Pauli and co-workers (Abdel-Ghany et al, 1998; Cheng et al, 1998; Cheng et al, 1999; Johnson et al, 1993) have demonstrated an important role of DPIV/Fibronectin binding in lung metastasis and have discussed the F344JAP rat as a "protein knock-out" model, although this substrain expresses mutant, enzymatically inactive DPIV on endothelial cell surfaces, albeit at greatly reduced levels when compared to expression of wild type DPIV (Cheng et al, 1999).

On the basis of these findings, the investigation of the role of DPIV expression and enzymic activity in cancer and cancer according to the present invention revealed the oral administration of DPIV inhibitors in results in a decrease of lung metastasis and colonization.

The goal of the present invention is the development of dipeptidyl peptidase IV inhibitors and/or ligands, which display a high bioavailability. In another preferred embodiment, the present invention provides DPIV inhibitors, which have an exactly predictable activity time in the target tissue.

Examples for target specific, orally available low molecular weight agents are prodrugs of stable and unstable dipeptidyl peptidase IV inhibitors which comprise general formula A-B—C, whereby A represents an amino acid, B represents the chemical bond between A and C or an amino acid, and C represents an unstable or a stable inhibitor of dipeptidyl peptidase IV respectively. They are described in WO 99/67278, WO 99/67279 the teachings of which are herein incorporated by reference in their entirety.

The present invention relates to a novel method, in which the reduction of activity in the enzyme dipeptidyl peptidase (DPIV or CD 26), or of DPIV-like enzyme activity, or where binding of a DPIV specific ligand exerts tumor suppressive or immunostimulating effects in the organisms of mammals induced by effectors of the enzyme leads as a causal consequence to a reduced growth or adhesion of cancer cells. Such treatment will result in a reduction or delay of cancer cell adhesion (metastasis) or the growth of tumor. As a consequence mammals bearing cancer will benefit from the treatment with inhibitors of DPIV a DPIV-like enzyme activity.

The method of the present invention for treating cancer in an animal, including humans, in need thereof, comprises anti-cancer effects by binding or by inhibiting DPIV, or related enzyme activities, using an inhibitor or ligand of these enzymes. Oral administration of a DPIV inhibitor may be preferable in most circumstances.

The present invention will now be illustrated with reference to the following examples focusing on the anti-cancer-like and anti-metastatic-like action of reduced DPIV-like activity and/or binding in an in vivo cancer cell adhesion assay (example 13), and in cancer colonization assays (example 14).

In one illustrative embodiment, the present invention relates to dipeptide compounds and compounds analogous to dipeptide compounds that are formed from an amino acid and a thiazolidine or pyrrolidine group, and salts thereof, referred to hereinafter as dipeptide compounds.

The use of such compounds as inhibitors of DPIV or of DPIV-analogous enzyme activity is already known from DD 296 075, PCT/DE 97/00820 and PCT/EP 99/03712.

Especially suitable for that purpose according to the invention are dipeptide compounds in which the amino acid is selected from a natural amino acid, such as, for example, leucine, valine, glutamine, glutamic acid, proline, isoleucine, asparagines and aspartic acid.

The dipeptide compounds according to the invention exhibit at a concentration (of dipeptide compounds) of 10 μM, especially under the conditions indicated in Table 1, a reduction in the activity of dipeptidyl peptidase IV or DPIV-analogous enzyme activities of at least 10%, especially of at least 40%. Frequently a reduction in activity of at least 60% or at least 70% is also required. Preferred effectors may also exhibit a reduction in activity of a maximum of 20% or 30%.

Preferred compounds are L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine of formulas 1 and 2:

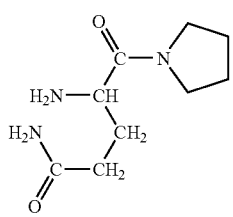

(1)

-continued

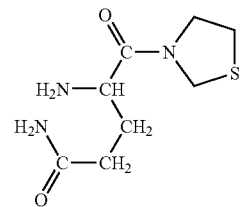

(2)

Further preferred compounds are given in Table 1. The salts of the dipeptide compounds can be present in a molar ration of dipeptide (-analogous) component to salt component of 1:1 or 2:1. Such a salt is, for example, (Ile-Thia)$_2$ fumaric acid.

TABLE 1

Structures of further preferred dipeptide compounds
Effector

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine In another preferred embodiment, the present invention provides peptide compounds of formula 3 useful for competitive modulation of dipeptidyl peptidase IV catalysis:

$$A\diagdown^B\diagdown_C\diagup^D\diagdown E \qquad (3)$$

wherein
A, B, C, D and E are any amino acid residues including proteinogenic amino acids, non-proteinogenic amino acids, L-amino acids and D-amino acids and wherein E and/or D may be absent or B and/or A may be absent with additional conditions as hereinafter detailed:

Further conditions regarding formula (3):

A is any amino acid residue except D-amino acid residues;

B is any proteinogenic amino acid residue, but

If B is an amino acid selected from Pro, Ala, Ser, Gly, Hyp, acetidine-(2)-carboxylic acid or pipecolic acid, then C is any amino acid residue including D-amino acids, except Pro, Ala, Ser, Gly, Hyp, acetidine-(2)-carboxylic acid or pipecolic acid and E may be unused to generate tetrapeptides of the formula A-B—C-D, or D and E may be unused to generate tripeptides of the formula A-B—C provided, but If B is not an amino acid selected from Pro, Ala, Ser, Gly, Hyp, acetidine-(2)-carboxylic acid or pipecolic acid, then C is any α-amino acid except D-amino acids; D is Pro, Ala, Ser, Gly, Hyp, acetidine-(2)-carboxylic acid or pipecolic acid; E is any amino acid residue including D-amino acids, except Pro, Ala, Ser, Gly, Hyp, acetidine-(2)-carboxylic acid or pipecolic acid, but If D is Pro, Ala, Ser, Gly, Hyp, acetidine-(2)-carboxylic acid or pipecolic acid, then C is any α-amino acid except D-amino acids and Pro, Ala, Ser, Gly, Hyp, acetidine-(2)-carboxylic acid or pipecolic acid, and A may be unused to generate tetrapeptides of the formula B—C-D-E, or A and B may be unused to generate tripeptides of the formula C-D-E provided however, If D is not selected from Pro, Ala, Ser, Gly, Hyp, acetidine-(2)-carboxylic acid or pipecolic acid, then E is any amino acid residue including D-amino acids.

Amino acid residues used for the preparation of the compounds of formula (3) can be generally subclassified into four major subclasses as follows.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or nonpolar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;

Basic/noncyclic: Arginine, Lysine;

Basic/cyclic: Histidine;

Neutral/polar/small: Glycine, Serine and Cysteine;

Neutral/polar/large/nonaromatic: Threonine, Asparagine, Glutamine;

Neutral/polar/large/aromatic: Tyrosine;

Neutral/nonpolar/small: Alanine;

Neutral/nonpolar/large/nonaromatic: Valine, Isoleucine, Leucine, Methionine;

Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this specific defined group.

Certain commonly encountered amino acids, which are not encoded by the genetic code, include, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO). These also fall conveniently into particular categories.

Based on the above definition,

Sar and beta-Ala are neutral/nonpolar/small;

t-butyl-Ala, t-butyl-Gly, N-MeIle, Nle and Cha are neutral/nonpolar/large/nonaromatic;

Har and Orn are basic/noncyclic;

Cya is acidic;

Cit, Acetyl-Lys, and MSO are neutral/polar/large/nonaromatic; and

Phg is neutral/nonpolar/large/aromatic.

The various omega-amino acids are classified according to size as neutral/nonpolar/small (beta-Ala, i.e., 3-aminopropionic, 4-aminobutyric) or large (all others).

Other amino acid substitutions for those encoded in the genetic code can also be included in peptide compounds within the scope of the invention and can be classified within this general scheme.

Proteinogenic amino acids are defined as natural protein-derived α-amino acids. Non-proteinogenic amino acids are defined as all other amino acids, which are not building blocks of common natural proteins.

The resulting peptides may be synthesized as the free C-terminal acid or as the C-terminal amide form. The free acid peptides or the amides may be varied by side chain modifications. Such side chain modifications include for instance, but not restricted to, homoserine formation, pyroglutamic acid formation, disulphide bond formation, deamidation of asparagine or glutamine residues, methylation, t-butylation, t-butyloxycarbonylation, 4-methylbenzylation, thioanysilation, thiocresylation, bencyloxymethylation, 4-nitrophenylation, bencyloxycarbonylation, 2-nitrobencoylation, 2-nitrosulphenylation, 4-toluenesulphonylation, pentafluorophenylation, diphenylmethylation, 2-chlorobenzyloxycarbonylation, 2,4,5-trichlorophenylation, 2-bromobenzyloxycarbonylation, 9-fluorenylmethyloxycarbonylation, triphenylmethylation, 2,2,5,7,8,-pentamethyl-chroman-6-sulphonylation, hydroxylation, oxidation of methionine, formylation, acetylation, anisylation, bencylation, bencoylation, trifluoroacetylation, carboxylation of aspartic acid or glutamic acid, phosphorylation, sulphation, cysteinylation, glycolysation with pentoses, deoxyhexoses, hexosamines, hexoses or N-acetylhexosamines, farnesylation, myristolysation, biotinylation, palmitoylation, stearoylation, geranylgeranylation, glutathionylation, 5'-adenosylation, ADP-ribosylation, modification with N-glycolylneuraminic acid, N-acetyineuraminic acid, pyridoxal phosphate, lipoic acid, 4'-phosphopantetheine, or N-hydroxysuccinimide.

In the compounds of formula (3), the amino acid residues comprising A, B, C, D, and E substituents are attached to the adjacent moiety according to standard nomenclature so that the amino-terminus (N-terminus) of the amino acids is drawn on the left and the carboxyl-terminus of the amino acid is drawn to the right.

Until the present invention by Applicants, known peptide substrates of the proline-specific serine protease dipeptidyl peptidase IV in vitro are the tripeptides Diprotin A (Ile-Pro-Ile), Diprotin B (Val-Pro-Leu) and Diprotin C (Val-Pro-Ile). Applicants have unexpectedly discovered that the compounds disclosed here act as substrates of dipeptidyl peptidase IV in vivo in a mammal and, in pharmacological doses, inhibit the physiological turnover of endogenous substrates by competitive catalysis.

Particularly preferred compounds of the present invention that could be useful as modulators of dipeptidyl peptidase IV and DPIV-like enzymes include those compounds which show $K_i$-values for DPIV-binding, effectively in DPIV-inhibition in vivo after i.v. and/or p.o. administration to Wistar rats Further preferred compounds according to the present invention are peptidylketones of formula 4:

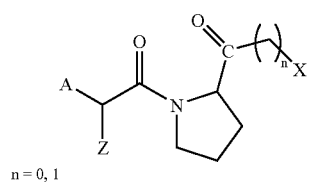

(4)

n = 0, 1 wherein
A is selected from:

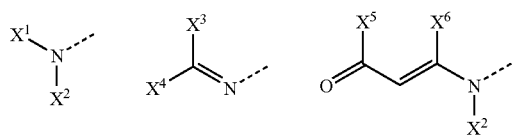

$X^1$ is H or a acyl or oxycarbonyl group incl. all amino acids and peptide residues, $X^2$ is H, $-(CH)_n-NH-C_5H_3N-Y$ with n=2-4 or $C_5H_3N-Y$ (a divalent pyridy residue) abd Y is selected from H, Br, Cl, I, $NO_2$ or CN, $X^3$ is H or selected from an alkyl, alkoxy, halogen, nitro, cyano or carboxy substituted phenyl or pyridyl residue, $X^4$ is H or selected from an alkyl, alkoxy, halogen, nitro, cyano or carboxy substituted phenyl or pyridyl residue, $X^5$ is H or an alkyl, alkoxy or phenyl residue, $X^6$ is H or a alkyl residue.

for n=1
X is selected from: H, $OR^2$, $SR^2$, $NR^2R^3$, $N^+R^2R^3R^4$, wherein:

$R^2$ stands for acyl residues, which are substituted with alkyl, cycloalkyl, aryl or heteroaryl residues, or for all amino acids and peptidic residues, or alkyl residues, which are substituted with alkyl, cycloalkyl, aryl and heteroaryl residues, $R^3$ stands for alkyl and acyl functions, wherein $R^2$ and $R^3$ may be embedded in ring structures of saturated and unsaturated carbocyclic or heterocyclic structures, $R^4$ stands for alkyl residues, wherein $R^2$ and $R^4$ or $R^3$ and $R^4$ may be embedded in ring structures of saturated and unsaturated carbocyclic or heterocyclic structures.

for n=0
X is selected from:

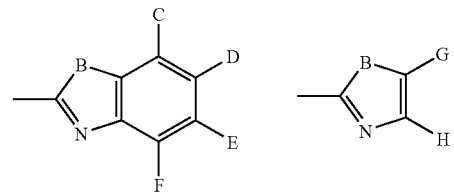

wherein
B stands for: O, S, $NR^5$, wherein $R^5$ is H, a alkyl or acyl,
C, D, E, F, G, H are independently selected from alkyl and substituted alkyl residues, oxyalkyl, thioalkyl, aminoalkyl, carbonylalkyl, acyl, carbamoyl, aryl and heteroaryl residues; and Z is selected from H, or a branched or single chain alkyl residue from $C_1$-$C_9$ or a branched or single chain alkenyl residue from $C_2$-$C_9$, a cycloalkyl residue from $C_3$-$C_8$, a cycloalkenyl residue from $C_5$-$C_7$, a aryl- or heteroaryl residue, or a side chain selected from all side chains of all natural amino acids or derivatives thereof.

Further, the present invention provides compounds of formulas 5, 6, 7, 8, 9, 10 and 11, including all stereoisomers and pharmaceutical acceptable salts thereof,

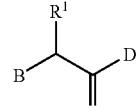

(5)

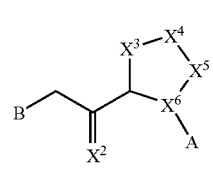

(6)

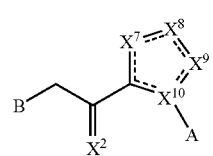

(7)

-continued

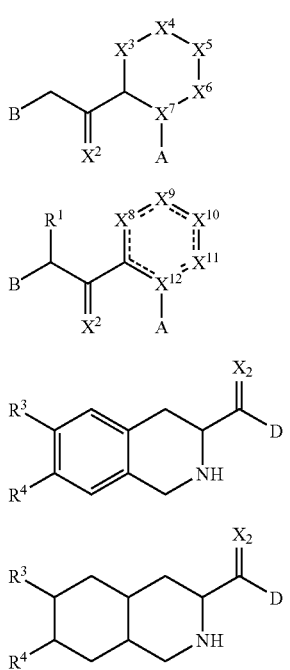

wherein:

$R^1$ is H, a branched or linear $C_1$-$C_9$ alkyl residue, a branched or linear $C_2$-$C_9$ alkenyl residue, a $C_3$-$C_8$ cycloalkyl-, $C_5$-$C_7$ cycloalkenyl-, aryl- or heteroaryl residue or a side chain of a natural amino acid or a derivative thereof, $R^3$ and $R^4$ are selected from H, hydroxy, alkyl, alkoxy, aryloxy, nitro, cyano or halogen, A is H or an isoster of an carbonic acid, like a functional group selected from CN, $SO_3H$, CONHOH, $PO_3R^5R^6$, tetrazole, amide, ester, anhydride, thiazole and imidazole, B is selected from:

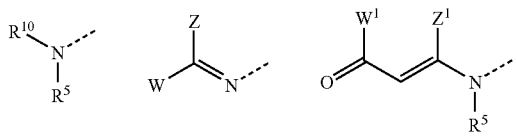

wherein:

$R^5$ is H, —(CH)$_n$—NH—$C_5H_3N$—Y with n=2-4 and $C_5H_3N$—Y (a divalent pyrid residue) with Y=H, Br, Cl, I, $NO_2$ CN, $R^{10}$ is H, a acyl, oxycarbonyl or a amino acid residue, W is H or a phenyl or pyridyl residue, substituted with alkyl, alkoxy, halogen, nitro, cyano or carboxy residue, $W^1$ is H, a alkyl, alkoxy or phenyl residue, Z is H or a phenyl or pyridyl residue, substituted with alkyl, alkoxy, halogen, nitro, cyano or carboxy residue, $Z^1$ is H or a alkyl residue, D is a cyclic $C_4$-$C_7$ alkyl, $C_4$-$C_7$ alkenyl residue or a alkyl substituted derivative thereof or a cyclic 4-7-membered heteroalkyl or 4-7-membered heteroalkenyl residue, $X^2$ is O, $NR^6$, $N^+(R^7)_2$, or S, $X^3$ to $X^{12}$ are selected from $CH_2$, $CR^8R^9$, $NR^6$, $N^+(R^7)_2$, O, S, SO and $SO_2$, including all saturated and unsaturated structures, $R^6$, $R^7$, $R^8$, $R^9$ are selected from H, a branched or linear $C_1$-$C_9$ alkyl residue, a branched or lienar $C_2$-$C_9$ alkenyl residue, a $C_3$-$C_8$ cycloalkyl residue, a $C_5$-$C_7$ cycloalkenyl residue, an aryl or heteroaryl residue, with the following provisions:

Formula 6: $X^6$ is CH if A is not H,

Formula 7: $X^{10}$ is C if A is not H,

Formula 8: $X^7$ is CH if A is not H,

Formula 9: $X^{12}$ is C if A is not H.

Because of the wide distribution of the protein in the body and the wide variety of mechanisms involving DPIV, DPIV-activity and DPIV-related proteins, systemic therapy (enteral or parenteral administration) with DPIV-inhibitors can result in a series of undesirable side-effects.

It has been possible to show that side chain-modified substrates of the enzyme dipeptidyl peptidase IV can be recognised by the enzyme and cleaved in the same way as unmodified substrates (DEMUTH, H.-U., HEINS, J., 1995).

For example, it has been possible to show that phosphorylated dipeptide-(B)-p-nitroanilides [KASPARI, A., et al., 1996] are substrates of DPIV. DPIV-inhibitors such as, for example, Glu(Gly)-Thia or Lys(Z-$NO_2$)-Thia [REINHOLD, D., et al., 1998] are transported completely.

The problem to be solved consisted in preparing compounds that can be used for targeted influencing of locally limited pathophysiological and physiological processes. The problem of the invention especially consists in obtaining locally limited inhibition of DPIV or DPIV-analogous activity for the purpose of targeted intervention in the regulation of the activity of locally active substrates.

This problem is solved according to the invention by providing compounds of the general formula (12)

wherein

A is an amino acid having at least one functional group in the side chain,

B is a chemical compound covalently bound to at least one functional group of the side chain of A, namely oligopeptides having a chain length of up to 20 amino acids, except for homopolymers of glycine consisting of up to 6 glycine monomers, or polyethylene glycols having molar masses of up to 20 000 g/mol, and C is a thiazolidine, pyrrolidine, cyanopyrrolidine, hydroxyproline, dehydroproline or piperidine group amide-bonded to A.

In accordance with the invention, pharmaceutical compositions are provided comprising at least one compound of the general formula (12)

(12)

wherein

A is an amino acid, preferably an α-amino acid, especially a natural α-amino acid having at least one functional group in the side chain, preferably threonine, tyrosine, serine, arginine, lysine, aspartic acid, glutamic acid or cysteine, B is a chemical compound covalently bound to at least one functional group in the side chain of A, namely oligopeptides having a chain length of up to 20 amino acids, polyethylene glycols having molar masses of up to 20 000 g/mol, optionally substituted organic amines, amides, alcohols, acids or aromatic compounds having from 8 to 50 C atoms, C is a thiazolidine, pyrrolidine, cyanopyrrolidine, hydroxyproline, dehydroproline or piperidine group amide-bonded to A, and at least one customary adjuvant appropriate for the site of action.

Throughout the description and the claims for the compounds of formula (12), the expression "alkyl" can denote a $C_{1-50}$ alkyl group, preferably a $C_{6-30}$ alkyl group, especially a $C_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-10}$ alkynyl group, preferably a $C_{2-6}$ alkynyl group, which has the triple bond(s) at any desired location and may be substituted or unsubstituted; the expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the aforementioned substituents may in turn have one or more (but preferably zero) alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae $(alkyl)_2N$— or alkyl-NH—, —CO—N(alkyl)$_2$ or —CO—NH(alkyl), -alkyl-OH or -alkyl-COOH.

Despite an extended side chain function, the compounds of formula (12) can still bind to the active centre of the enzyme dipeptidyl peptidase IV and analogous enzymes but are no longer actively transported by the peptide transporter PepT1. The resulting reduced or greatly restricted transportability of the compounds according to the invention leads, in ideal manner, to local or site directed inhibition of DPIV and DPIV-like enzyme activity.

The compounds of formula (12) or compounds used in accordance with the invention can be present or used, respectively, in the form of racemates or in the form of enantiomerically pure compounds, preferably in the L-threo or L-allo form with respect to part A of formula (12).

By extending/expanding the side chain modifications, for example beyond a number of seven carbon atoms, it is accordingly possible to obtain a dramatic reduction in transportability (see Example 12). The Examples in Table 12.1 clearly show that, with increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

According to the present invention, the compounds of formula (12) inhibit DPIV or DPIV-like enzyme activity in the body of a mammal in a site specific manner. It is accordingly possible to influence local physiological and pathophysiological conditions (inflammation, psoriasis, arthritis, autoimmune diseases, allergies) effectively and with dramatically reduced side-effects.

Preferred compounds of formula (12) are compounds, wherein the oligopeptides have chain lengths of from 3 to 15, especially from 4 to 10, amino acids, and/or the polyethylene glycols have molar masses of at least 250 g/mol, preferably of at least 1500 g/mol and up to 15 000 g/mol, and/or the optionally substituted organic amines, amides, alcohols, acids or aromatic compounds have at least 12 C atoms and preferably up to 30 C atoms.

The compounds of the present invention can be converted into acid addition salts, especially pharmaceutically acceptable acid addition salts. The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of formulas (1) to (12) are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113 and DE 198 28 114, which are fully incorporated herein by reference.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

As indicated above, the compounds of the present invention, and their corresponding pharmaceutically acceptable acid addition salt forms, are useful in inhibiting DPIV and DPIV-like enzyme activity. The ability of the compounds of the present invention, and their corresponding pharmaceutically acceptable acid addition salt forms to inhibit DPIV and DPIV-like enzyme activity may be demonstrated employing the DPIV activity assay for determination of the $K_i$-values and the $IC_{50}$-values in vitro, as described in examples 7 and 8.

The ability of the compounds of the present invention, and their corresponding pharmaceutically acceptable acid addition salt forms to inhibit DPIV in vivo may be demonstrated by oral or intravasal administration to Wistar rats, as described in example 11. The compounds of the present invention inhibit DPIV activity in vivo after both, oral and intravasal administration to Wistar rats.

DPIV is present in a wide variety of mammalian organs and tissues e.g. the intestinal brush-border (Gutschmidt S. et al., "In situ"—measurements of protein contents in the brush border region along rat jejunal villi and their correlations with four enzyme activities. Histochemistry 1981, 72 (3), 467-79), exocrine epithelia, hepatocytes, renal tubuli, endothelia, myofibroblasts (Feller A. C. et al., A monoclonal antibody detecting dipeptidylpeptidase IV in human tissue. Virchows Arch. A. Pathol. Anat. Histopathol. 1986; 409 (2):263-73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151-61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435-52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486-96). The serum high molecular weight form of DPIV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714-21).

The compounds of the present invention, and their corresponding pharmaceutically acceptable acid addition salt forms are able to inhibit DPIV in vivo. In one embodiment of the present invention, all molecular forms, homologues and epitopes of DPIV from all mammalian tissues and organs, also of those, which are undiscovered yet, are intended to be embraced by the scope of this invention.

Among the rare group of proline-specific proteases, DPIV was originally believed to be the only membrane-bound enzyme specific for proline as the penultimate residue at the amino-terminus of the polypeptide chain. However, other molecules, even structurally non-homologous with the DPIV but bearing corresponding enzyme activity, have been identified recently. DPIV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? Biochimica et Biophysica Acta 2001, 36506: 1-10). Further DPIV like enzymes are disclosed in WO 01/19866, WO 02/04610 and WO 02/34900. WO 01/19866 discloses novel human dipeptidyl aminopeptidase (DPP8) with structural und functional similarities to DPIV and fibroblast activation protein (FAP). The dipeptidyl peptidase IV-like enzyme of WO 02/04610 is well known in the art. In the Gene Bank data base, this enzyme is registered as KIAA1492. In another preferred embodiment of the present invention, all molecular forms, homologues and epitopes of proteins comprising DPIV-like enzyme activity, from all mammalian tissues and organs, also of those, which are undiscovered yet, are intended to be embraced by the scope of this invention.

The ability of the compounds of the present invention, and their corresponding pharmaceutically acceptable acid addition salt forms to inhibit DPIV-like enzymes may be demonstrated employing an enzyme activity assay for determination of the $K_i$-values in vitro as described in example 9. The $K_i$-values of the compounds of the present invention against porcine dipeptidyl peptidase II were exemplary determined as $K_i=8.52*10^{-5}$ M±6.33*10$^{-6}$ M for glutaminyl pyrrolidine and $K_i=1.07*10^{-5}$ M±3.81*10$^{-7}$M for glutaminyl thiazolidine.

In another embodiment, the compounds of the present invention, and their corresponding pharmaceutically acceptable acid addition salt forms have only low, if no inhibitory activity against non-DPIV and non-DPIV-like proline specific enzymes. As described in example 10, with glutaminyl thiazolidine and glutaminyl pyrrolidine exemplarily, no inhibition of dipeptidyl peptidase I and prolyl oligopeptidase was found. Against prolidase, both compounds explained a marked lower efficacy compared to DPIV. The IC 50-values against prolidase were determined as IC 50>3 mM for glutaminyl thiazolidine and as IC 50=3.4*10$^{-4}$M ±5.63*10$^{-5}$ for glutaminyl pyrrolidine.

The present invention provides a method of treating a condition mediated by modulation of the DPIV or DPIV-like enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the treatment of a condition mediated by modulation of the DPIV activity in a subject. The compound may be administered to a patient by any conventional route of administration, including, but not limited to, intravenous, oral, subcutaneous, intramuscular, intradermal and parenteral.

In a further illustrative embodiment, the present invention provides formulations for the compounds of formulas 1 to 12, and their corresponding pharmaceutically acceptable acid addition salt forms, in pharmaceutical compositions.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "composition" is intended to encompass a product comprising the claimed compounds in the therapeutically effective amounts, as well as any product which results, directly or indirectly, from combinations of the claimed compounds.

To prepare the pharmaceutical compositions of this invention, one or more compounds of formulas 1 to 12, and their corresponding pharmaceutically acceptable acid addition salt forms, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar coated or enteric coated by standard techniques. For parenterals the carrier will usually comprise sterile water, through other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit a dosage unit, e.g., tablet, capsule, powder, injection, suppository, teaspoonful and the like, of from about 0.03 mg to 100 mg/kg (preferably 0.1-30 mg/kg) and may be given at a dosage of from about 0.1-300 mg/kg per day (preferably 1-50 mg/kg per day). The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from 0.1 to about 500 mg of the active ingredient of the present invention.

The tablets or pills of the novel composition can be advantageously coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

This liquid forms in which the novel compositions of the present invention may be advantageously incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991, fully incorporated herein by reference. The protecting groups may be removed at a convenient subsequent stage using methods known from the art.

The method of treating conditions modulated by dipeptidyl peptidase IV and DPIV-like enzymes described in the present invention may also be carried out using a pharmaceutical composition comprising any of the compounds as defined herein and a pharmaceutically acceptable carrier. The pharmaceutical composition may contain between about 0.01 mg and 1000 mg, preferably about 5 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds of the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

More preferably, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and other compounds known within the art.

The liquid forms are suitable in flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl eneoxidepolyllysine substituted with palmitoyl residue. Furthermore, compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

EXAMPLES

Example 1

Synthesis of Dipeptide Compounds 1.1 General Synthesis of Isoleucyl Thiazolidine Salt The Boc-protected amino acid BOC-Ile-OH is placed in ethyl acetate and the batch is cooled to about −5° C. N-Methylmorpholine is added dropwise, pivalic acid chloride (on a laboratory scale) or neohexanoyl chloride (on a pilot-plant scale) is added dropwise at constant temperature. The reaction is stirred for a few minutes for activation. N-Methylmorpholine (laboratory scale) and thiazolidine hydrochloride (laboratory scale) are added dropwise in succession, thiazolidine (pilot-plant scale) is added. Working-up in the laboratory is effected in conventional manner using salt solutions, on a pilot-plant scale the batch is purified with NaOH and $CH_3COOH$ solutions.

The removal of the BOC protecting group is carried out using HCl/dioxane (laboratory scale) or $H_2SO_4$ (pilot-plant scale). In the laboratory the hydrochloride is crystallised from EtOH/ether.

On a pilot-plant scale the free amine is prepared by the addition of $NaOH/NH_3$. Fumaric acid is dissolved in hot ethanol, the free amine is added dropwise, and (Ile-Thia)$^2$ fumarate (M=520.71 gmol$^{-1}$) precipitates. The analysis of isomers and enantiomers is carried out by electrophoresis.

1.2 Synthesis of Glutaminyl Pyrrolidine Free Base

Acylation:

N-Benzyl-oxycarbonylglutamine (2.02 g, 7.21 mmol) was dissolved in 35 ml THF and brought to −15° C. Into that mixture CAIBE (isobutylchloroformiate) (0.937 ml, 7.21 mmol) and 4-methylmorpholine (0.795 ml, 7.21 mmol) where added and the solution was stirred for 15 min. The formation of the mixed anhydride was checked by TLC (eluent: $CHCl_3$/MeOH: 9/1). After warming to −10° C. pyrrolidine (0.596 ml, 7.21 mmol) was added. The mixture was brought to room temperature and stirred overnight.

Workup:

The sediment formed was filtered off and the solvent was evaporated. The resulting oil was taken up in ethylacetate (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 1.18 g, waxy solid

Cleavage:

1.18 g of the resulting solid Z-protected compound was dissolved in 40 ml absolute ethanol. Into the solution ca. 20 mg Pd on charcoal (10%, FLUKA) was added and the suspension was shaken under a hydrogen atmosphere for 3 h. The progress of the reaction was monitored by TLC (eluent: $CHCl_3$/MeOH: 9/1). After completion of the reaction the was removed to provide the free base.

Yield: 99%

The purity was checked by means of TLC: n-butanole/AcOH/water/ethylacetate: 1/1/1/1, $R_f$=0.4. The identity of the reaction product was checked by NMR analysis.

1.3 Synthesis of Glutaminyl Thiazolidine Hydrochloride

Acylation:

N-t-Butyl-oxycarbonylglutamine (2.0 g, 8.12 mmol) was dissolved in 5 ml THF and brought to −15° C. Into that mixture CAIBE (isobutylchloroformiate) (1,06 ml, 8.12 mmol) and 4-methylmorpholine (0.895 ml, 8.12 mmol) where added and the solution was stirred for 15 min. The formation of the mixed anhydride was checked by TLC (eluent: $CHCl_3$/MeOH: 9/1). After warming to −10° C. another equivalent 4-methylmorpholine (0.895 ml, 8.12 mmol) and thiazolidinehydrochloride (1.02 g, 8.12 mmol was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 1.64 g, solid

Cleavage:

640 mg of the resulting solid Boc-protected compound was dissolved in 3.1 ml ice cold HCl in dioxane (12.98 M, 20 equivalents) and left on ice. The progress of the reaction was monitored by TLC (eluent: $CHCl_3$/MeOH: 9/1). After completion of the reaction the solvent was removed and the resulting oil was taken up in methanole and evaporated again. After that the resulting oil was dried over phosphorous-V-oxide and triturated two times with diethylether. The purity was checked by HPLC.

Yield: 0.265 g

The purity was checked by HPLC. The identity of the reaction product was checked by NMR analysis.

1.4 Synthesis of Glutaminyl Pyrrolidine Hydrochloride

Acylation:

N-t-Butyl-oxycarbonylglutamine (3.0 g, 12.18 mmol) was dissolved in 7 ml THF and brought to −15° C. Into that mixture CAIBE (isobutylchloroformiate) (1,6 ml, 12.18 mmol) and 4-methylmorpholine (1.3 ml, 12.18 mmol) where added and the solution was stirred for 15 min. The formation of the mixed anhydride was checked by TLC (eluent: $CHCl_3$/MeOH: 9/1). After warming to −10° C. 1 equivalent of pyrrolidine (1.0 ml, 12.18 mmol) was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 2.7 g solid

Cleavage:

2.7 g of the resulting solid was dissolved in 13.0 ml ice cold HCl in dioxane (12.98 M, 20 equivalents) and left on ice. The progress of the reaction was monitored by TLC (eluent: $CHCl_3$/MeOH: 9/1). After completion of the reaction the solvent was removed and the resulting oil was taken up in methanole and evaporated again. After that the resulting oil was dried over phosphorous-V-oxide and triturated two times with diethylether.

Yield: 980 mg

The purity was checked by HPLC. The identity of the reaction product was checked by NMR analysis.

Example 2

Chemical Characterization of Selected Dipeptide Compounds

2.1 Melting Point Determination

Melting points were determined on a Kofler heating platform microscope from Leica Aktiengesellschaft, the values are not corrected, or on a DSC apparatus (Heumann-Pharma).

2.2 Optical Rotation

The rotation values were recorded at different wavelengths on a "Polarimeter 341" or higher, from the Perkin-Elmer company.

2.3 Measurement Conditions for the Mass Spectroscopy

The mass spectra were recorded by means of electrospray ionisation (ESI) on an "API 165" or API 365" from the PE Sciex company. The operation is carried out using an approximate concentration of c=10 µg/ml, the substance is taken up in MeOH/$H_2O$ 50:50, 0.1% $HCO_2H$, the infusion is effected using a spray pump (20 µl/min). The measurement were made in positive mode [M+H]$^+$, the ESI voltage is U=5600V.

2.4. Results

2.4.1 Tests on Isoleucyl Thiazolidine Fumarate (Isomer)

| Substance | Mp (° C.) | CE (min) | MS | [α] $H_2O$ |
|---|---|---|---|---|
| L-threo-IT*F | 150$^{DSC}$ | 160 | 203 | −10.7 (405 nm) |
| D-threo-IT*F | 147 | 158 | 203 | not determined |
| L-allo-IT*F | 145-6 | 154 | 203 | −4.58 (380 nm) |
| D-allo-IT*F | 144-6 | 150 | 203 | 4.5 (380 nm) |

IT*F = isoleucyl thiazolidine fumarate

The NMR and HPLC data confirm the identity of the substance in question.

2.4.2 Tests on Other Isoleucyl Thiazolidine Salts

| IT*salt | M (gmol$^{-1}$) | MP (° C.) |
|---|---|---|
| succinate | 522.73 | 116 |
| tartrate | 352.41 | 122 |
| fumarate | 520.71 | 156 |
| hydrochloride | 238.77 | 169 |
| phosphate | 300.32 | 105 |

Example 3

Synthesis of Xaa-Pro-Yaa Tripeptides

All syntheses were carried out on a peptide synthesizer SP 650 (Labortec AG) applying Fmoc/tBu-strategy. Protected amino acids were purchased from Novabiochem or Bachem. trifluoro acetic acid (TFA) was purchased from Merck, triisopropyl silane (TIS) was purchased from Fluka.

Pre-loaded Fmoc-Yaa-Wang resin (2.8 g/substitution level 0.57 mmol/g) was deprotected using 20% piperidine/N,N-dimethylformamide (DMF). After washing with DMF a solution of 2 eq (1.1 g) of Fmoc-Pro-OH were solved in DMF (12 ml solvent per gram resin). 2 eq (1.04 g) of 2-(1H-Benzotriazole 1-yl)-1,1,3,3-tetramethyluronium tetrafluoroborate (TBTU) and 4 eq (1.11 ml) of N,N-diisopropylethylamine (DIEA) were added and placed in the reaction vessel. The mixture was shaken at room temperature for 20 minutes. Then the coupling cycle was repeated. After subsequent washing with DMF, dichlormethane, isopropanol and diethyl ether the resulting Fmoc-Pro-Ile-Wang resin was dried and then divided into 6 parts before coupling the last amino acid derivative.

Fmoc protecting group was removed as described above. After that 0.54 mmol of the Boc-amino acid, 0.54 mmol TBTU and 0.108 mmol DIEA in DMF were shaken for 20 min. The coupling cycle was repeated. Finally the peptide resin was washed and dried described above.

The peptide was cleaved from the resin using a mixture of trifluoroacetic acid (TFA) for 2.5 h, containing the following scavengers: TFA/$H_2O$/triisipropylsilane (TIS)=9.5/0.25/0.25

The yields of crude peptides were 80-90% on the average. The crude peptide was purified by HPLC on a Nucleosil C18 column (7 µm, 250*21.20 mm, 100 A) using a linear gradient of 0.1% TFA/$H_2O$ with increasing concentration of 0.1% TFA/acetonitrile (from 5% to 65% in 40 min) at 6 ml/min.

The pure peptide was obtained by lyophilization, identified by Electrospray mass spectrometry and HPLC analysis.

3.1 Results—Identification of Xaa-Pro-Yaa Tripeptides after Chemical Synthesis

| Peptide | Mass (calc.) | Mass (exp.)[1] [M + H$^+$] | HPLC k'[2] |
|---|---|---|---|
| Abu-Pro-Ile | 313.4 | 314.0 | 5.7 |
| Cha-Pro-Ile | 381.52 | 382.0 | 10.4 |
| Nva-Pro-Ile | 327.43 | 328.2 | 6.82 |
| Phg-Pro-Ile | 361.44 | 362.2 | 7.9 |
| Nle-Pro-Ile | 341.45 | 342.2 | 8.09 |
| Pip-Pro-Ile | 338.56 | 340.0 | 6.5 |
| Thr-Pro-Ile | 329.4 | 330.0 | 5.12 |
| Trp-Pro-Ile | 414.51 | 415.2 | 9.85 |
| Phe-Pro-Ile | 375.47 | 376.2 | 8.96 |
| Ser-Pro-Ile | 315.37 | 316.3 | 5.24 |
| Ser(P)-Pro-Ile | 395.37 | 396.0 | 3.35 |
| Tyr(P)-Pro-Ile | 471.47 | 472.3 | 5.14 |
| Val-Pro-Val | 313.4 | 314.0 | 5.07 |
| Ile-Pro-Val | 327.43 | 328.5 | 6.41 |
| Ile-Pro-allo-Ile | 341.4 | 342.0 | 7.72 |
| Val-Pro-allo-Ile | 327.4 | 328.5 | 6.51 |
| Tyr-Pro-allo-Ile | 391.5 | 392.0 | 7.02 |
| 2-Amino octanoic acid-Pro-Ile | 369.5 | 370.2 | 10.63 |
| Ser(Bzl)-Pro-Ile | 405.49 | 406.0 | 9.87 |
| Orn-Pro-Ile | 342.42 | 343.1 | 3.73 |
| Tic-Pro-Ile | 387.46 | 388.0 | 8.57 |
| Aze-Pro-Ile | 311.4 | 312.4 | 5.29 |
| Aib-Pro-Ile | 313.4 | 314.0 | 5.25 |
| t-butyl-Gly-Pro-Ile | 341.47 | 342.1 | 7.16 |
| Ile-Hyp-Ile | 356.45 | 358.2 | 6.57 |
| t-butyl-Gly-Pro-Val | 327.4 | 328.4 | 6.32 |
| t-butyl-Gly-Pro-Gly | 285.4 | 286.3 | 3.74 |
| t-butyl-Gly-Pro-Ile-amide | 340.47 | 341.3 | 7.8 |
| t-butyl Gly-Pro-D-Val | 327.4 | 328.6 | 7.27 |
| t-butyl-Gly-Pro-t-butyl-Gly | 341.24 | 342.5 | 9.09 |
| Ile-Pro-t-butyl-Gly | 341.47 | 342.36 | 6.93 |
| Val-Pro-t-butyl-Gly | 327.4 | 328.15 | 5.98 |

[1] [M + H$^+$] were determined by Electrospray mass spectrometry in positive ionization mode.
[2] RP-HPLC conditions:
column: LiChrospher 100 RP 18 (5µm), 125 × 4 mm
detection (UV): 214 nm
gradient system: acetonitrile (ACN)/$H_2O$ (0.1% TFA) from 5% ACN to 50% in 15 min,
flow: 1 ml/min
k' = $(t_r-t_0)/t_0$
$t_0$ = 1.16 min
t-butyl-Gly is defined as:

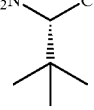

Ser(Bzl) and Ser(P) are defined as benzylserine and phosphorylserine, respectively. Tyr(P) is defined as phosphoryltyrosine.

Example 4
Synthesis of Peptidylketones
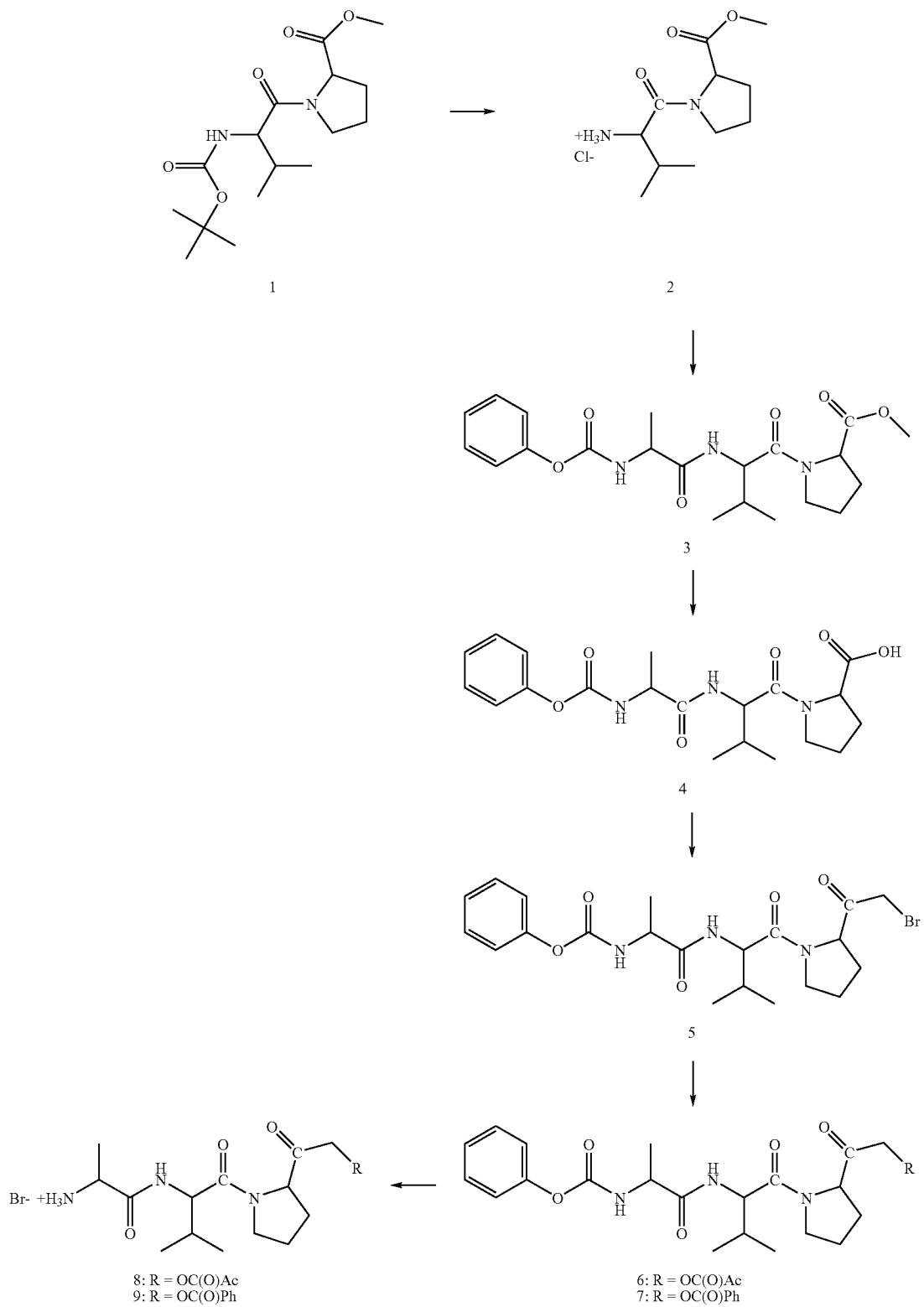

H-Val-Pro-OMe.HCl 2

Boc-Val-OH (3.00 g, 13.8 mmol) was dissolved in 10 ml of dry THF and cooled down to −15° C. To the mixture CAIBE (1.80 ml, 13.8 mmol) and NMM (1.52 ml, 13.8 mmol) where added and the solution was stirred until the formation of the mixed anhydride was complete. Then the mixture was brought to −10° C. and NMM (1.52 ml, 13.8 mmol) was added followed by H-Pro-OMe.HCl (2.29 g, 13.8 mmol). The mixture was allowed to reach room temperature and left overnight. After removing the solvent and the usual workup the resulting ester 1 was taken without further characterisation. The ester 1 was dissolved in HCl/HOAc (5 ml, 6N) and left at 0° C. until the removal of the Boc-group was complete. The solvent was then removed and the resulting oil was treated with diethylether to give a white solid 2.

Yield: 2.5 g, 80%

Z-Ala-Val-Pro-OMe 3

Z-Ala OH (3.5 g, 15.7 mmol) and 2 (4.18 g, 15.7 mmol) where treated in the same manner as above for 1, to give 3 as a white solid.

Yield: 4.2 g, 64%

Z-Ala-Val-Pro-OH 4

3 (4.2 g, 9.6 mmol) was dissolved in 30 ml of water/acetone (1/5 v/v) and 11.6 ml NaOH (1N) where added. After completion of the reaction the organic solvent was removed by evaporation and the resulting solution was diluted by 15 ml $NaHCO_3$ solution (saturated). Then the mixture was extracted three times by 10 ml of acetic acid ethyl ester. After that the solution was brought to pH2 by adding HCl (15% in water). The resulting mixture was extracted three times by 30 ml of acetic acid ethyl ester. The organic layer was separated and washed three times with brine, dried ($Na_2SO_4$) and evaporated.

Yield: 3.5 g, 87%

Z-Ala-Val-Pro-$CH_2$—Br 5

4 (2.00 g, 4.76 mmol) was dissolved in 15 ml of dry THF and converted into a mixed anhydride (see compound 1) using CAIBE (0.623 ml, 4.76 mmol) and NMM (0.525 ml, 4.76 mmol). The precipitate formed was filtered off and cooled down to −15° C. Then diazomethane (23.8 mmol in 30 ml ether) was dropped into the solution under an argon atmosphere. After leaving the mixture for 1 h at 0° C. 1.27 ml of HBr (33% in AcOH) was added and the solution was stirred for 30 min at room temperature. After that 70 ml of ether was added and the mixture was washed with 20 ml of water. The organic layer was separated and dried ($Na_2SO_4$) and evaporated.

Yield (crude): 1.8 g, 80%

Z-Protected Acyloxymethylene Ketones

The acid (2 eq) was dissolved in DMF and an equimolar amount of KF was added. The suspension was allowed to stir at room temperature for 1 hour. Then the brommethylene (1 eq) component was added and the solution was allowed to stir overnight. After that the solvent was removed under vacuum and the resulting oil was dissolved in chloroform and washed with brine. Then the organic layer was separated dried ($Na_2SO_4$) and the solvent was removed. The product was purified by column chromatography using silica gel and heptane/chloroform.

Z-Ala-Val-Pro-$CH_2$O—C(O)—$CH_3$ 6

Acetic acid (230 μl, 4.02 mmol), KF (0.234 g, 4.02 mmol), 5 (1.00 g, 2.01 mmol)

Yield: 0.351 g, 36%

Z-Ala-Val-Pro-$CH_2$O—C(O)—Ph 7

Benzoic acid (0.275 g, 2.25 mmol), KF (0.131 mg, 2.25 mmol), 5 (0.56 g. 1.13 mmol)

Yield: 0.34 g, 56%

Deprotection

The Z-protected compound was dissolved in HBr/AcOH and stirred. When the reaction was complete ether was added, the white precipitate formed was filtered off and dried.

H-Ala-Val-Pro-$CH_2$O—C(O)$CH_3$.HBr 8

6 (0.351 g, 0,73 mmol)

Yield: 0.252 g, 98%

H-Ala-Val-Pro-$CH_2$O—C(O)Ph.HBr 9

7 (0.34 g, 0.63 mmol)

Yield: 0.251 g, 99%

Example 5

Synthesis of Cycloalkylketones

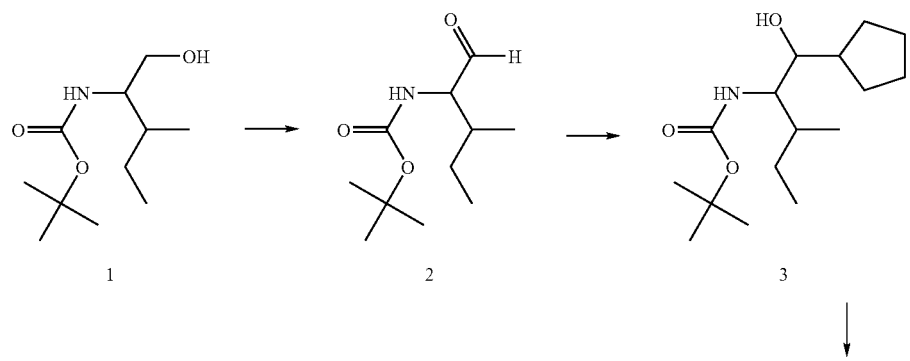

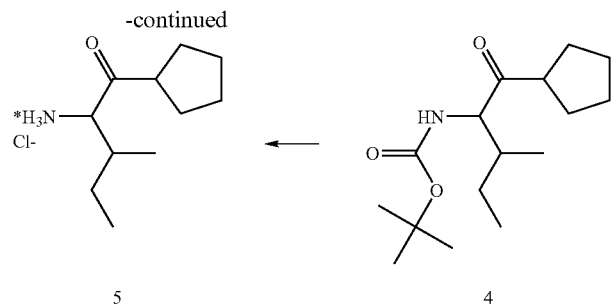

Boc-Isoleucinal 2

Oxalylchloride (714 μl, 8.28 mmol) was dissolved in 10 ml of dry dichlormethane and brought to −78° C. Then DMSO (817 μl, 8.28 mmol) was added dropwise. The solution was stirred for 20 min at −78° C. Then 1 (1.00 g, 4.6 mmol) was added and the mixture was stirred for 20 min. After that TEA (2.58 ml, 18.4 mmol) was added and the mixture was allowed to reach room temperature. The mixture was diluted with hexane/ethylacetate (2/1 v/v) and 10 ml of HCl (10% in water) was added. The organic layer was separated and the aqueous phase was extracted with 20 ml of methylenechloride. All organic layers were collected and washed with brine, followed by water, then dried. The product was purified by column chromatography using silica gel and heptane/chloroform.

Yield: 0.52 g, 52% tert-butyl N-1-[cyclopentyl(hydroxy)methyl]-2-methylbutylcarbamate 3

2 (0.52 g, 2.42 mmol) was dissolved in 10 ml of dry THF and cooled down to 0° C. Then cyclopentylmagnesiumbromide (1.45 ml of a 2 M solution) was added. After completion of the reaction (2 ml) of water was added and solution was neutralized by adding aqueous HCl. Then methylenechloride was added and the organic layer was separated and dried ($Na_2SO_4$). After evaporation the resulting oil was used without further characterisation.

tert-butyl N-[1-(cyclopentylcarbonyl)-2-methylbutyl]carbamate 4

3 (0.61 g, 2.15 mmol) was treated like 1. Oxalylchloride (333 μl, 3.87 mmol), DMSO (382 μl, 5.37 mmol), TEA (1.2 ml, 8.59 mmol)

Yield: 0.180 g, 30%

1-cyclopentyl-3-methyl-1-oxo-2-pentanaminium chloride 5

4 (0.18 g, 0.63 mmol) was dissolved in 2 ml HCl (7 N in dioxane). After completion of the reaction the solvent was removed and the resulting oil was purified by column chromatography on silical gel using a chloroform/methanol/water gradient. The resulting oil was triturated with ether.

Yield: 0.060 g, 54%

Example 6

Synthesis of Side Chain Modified DPIV-Inhibitors 6.1 Synthesis of Boc-Glutamyl-Thiazolidine (Boc-Glu-Thia)

Reaction of Boc-Glu(OMe)-OH with Thia.HCl according to Method B (see section 6.4 for methods), hydrolysis of Boc-Glu(OMe)-Thia according to Method G 6.1.1 Analytical Data for Boc-Glu-Thia

| Compound | Empirical formula $M_r$ Synthesis method Yield | MS $[M + H]^+$ TLC: $R_f$/system m.p. | $[α]^{20}D$ Concentration Solvent | Elemental analysis (calc./ found) % | HPLC $R_t$ [min]/system |
|---|---|---|---|---|---|
| Boc-Glu-Thia | $C_{13}H_{22}N_2O_5S$ 318.38 B + G 62% | 319.5 0.52/A[1] 0.42/B[1] 115-118° C. | −3.1 c = 1 methanol | C: 49.04/48.89 H: 6.96/6.82 N: 8.80/8.59 | 13.93/ A[2] |

[1]Thin-layer chromatography System A: chloroform/methanol 90:10 System B: benzene/acetone/acetic acid 25:10:0.5 System C: n-butanol/EA/acetic acid/$H_2O$ 1:1:1:1
[2]HPLC separation conditions Column: Nucleosil C-18, 7μ, 250 mm × 21 mm Eluant: isocratic, 40% ACN/water/0.1% TFA Flow rate: 6 ml/min λ = 220 nm 6.2 Side Chain-Modified Boc-Glutamyl Thiazolidines Boc-Glu-Thia was modified at the γ-carboxylic acid function by introducing radicals of varying size. The radicals were coupled by way of their amino group by forming an amide bond to the γ-carboxylic acid function, with a variety of coupling methods being used depending on the radical. The following amino components were attached to Boc-Glu-Thia using the method stated:

| Amino component | Coupling methods (see section 3.4) | Yields |
|---|---|---|
| Polyethylene glycol amine ($M_r \approx 8000$) | C | 93% |
| H-Gly-Gly-Gly-OH | D + E | 49% |
| H-Gly-Gly-Gly-Gly-Gly-OH | D + E | 86% |

In 2 cases, purification of the reaction products differs from the general description of synthesis.

Boc-Glu(Gly$_5$)-Thia

The product already precipitates out from the mixture on stirring overnight; it is subsequently filtered off and washed with 0.1N HCl and copious amounts of water and then dried over $P_4O_{10}$ in vacuo.

Boc-Glu(PEG)-Thia

In contrast to the general procedure, the starting materials for the synthesis are dissolved in a 500-fold excess of DMF. After the reaction is complete, the DMF is completely removed in vacuo and the residue is dissolved in a large amount of methanol. After ether is poured on, to form an upper layer, the product precipitates out together with the unreacted PEG. Fine purification was carried out by preparative HPLC separation on a gel filtration column (Pharmazia, Sephadex G-25, 90 μm, 260 mm-100 mm).

Separating conditions: eluant: water; flow rate: 5 ml/min; λ=220 nm

6.2.2 Synthesis Data for Side Chain-Modified Boc-Glutamyl Thiazolidines

| Compound Yield | Empirical formula $M_r$ | MS $[M + H]^+$ TLC/$R_f$/ system m.p. | $[\alpha]^{20}D$ Concentration Solvent | Elemental analysis (calc./ found) % | HPLC $R_t$ [min]/system |
|---|---|---|---|---|---|
| Boc-Glu(Gly$_3$)-Thia 49% | $C_{19}H_{31}N_5O_8S$ 489.54 | 490.5 | | C: 46.62 H: 6.38 N: 14.31 | |
| Boc-Glu(Gly$_5$)-Thia 86% | $C_{23}H_{37}N_7O_{10}S$ 603.64 | 604.5 0.09/C decomp. from 202° C. | n.dm. | C: 45.76/45.60 H: 6.18/6.11 N: 16.24/16.56 | 11.93/A$^2$ |
| Boc-Glu(PEG)-Thia 93% | | ≈8000 (mass emphasis) 52-53° C. | n.dm. | n.dm. | n.dm. |

$^2$HPLC separation conditions Column: Nucleosil C-18, 7μ, 250 mm × 21 mm Eluant: isocratic, 40% ACN/water/0.1% TFA Flow rate: 6 ml/min λ = 220 nm

6.3 Side Chain-Modified Glutamyl Thiazolidines

The N-terminal Boc protecting groups were cleaved off the compounds described in Table 6.2.2 using method F. The substances modified with Gly derivatives were purified by preparative HPLC separation and are present as trifluoroacetates. The H-Glu(PEG)-Thia was purified on a gel filtration column in the same manner as the Boc-protected precursor.

6.3.1 Synthesis Data for Side Chain-Modified Glutamyl Thiazolidines

| Compound Yield | Empirical formula $M_r$ | MS $[M + H]^+$ TLC/$R_f$/ system m.p. | $[\alpha]^{20}D$ Concentration Solvent | Elemental analysis (calc./ found) % | HPLC $R_t$ [min]/ system |
|---|---|---|---|---|---|
| H-Glu(Gly$_3$)-Thia *TFA 94% | $C_{16}H_{24}N_5O_8SF_3$ 503.45 | 503.45 0.32/C 91-94° C. | +4.1 c = 1 methanol | C: 38.17/37.56 H: 4.80/4.78 N: 13.91/13.43 | 7.84/C$^3$ |
| H-Glu(Gly$_5$)-Thia *TFA 98% | $C_{20}H_{30}N_7O_{10}SF_3$ 617.55 | 617.55 0.25/C 105-107° C. | n.dm. | C: 38.90/38.82 H: 4.90/4.79 N: 15.88/15.39 | 8.22/C$^3$ |
| H- 92% | | ≈8000 | n.dm. | n.dm. | n.dm. |

-continued

| Compound | Empirical formula $M_r$ Yield | MS $[M + H]^+$ TLC/$R_f$/ system m.p. | $[\alpha]^{20}$D Concentration Solvent | Elemental analysis (calc./ found) % | HPLC $R_t$ [min]/ system |
|---|---|---|---|---|---|
| Glu(PEG)-Thia *HCl | | (mass emphasis) | | | |

[3] HPLC separation conditions Column: Nucleosil C-18, 7μ, 250 mm × 21 mm Eluant: ACN/water/0.1% TFA Gradient: 20% ACN → 90% ACN over 30 min Flow rate: 6 ml/min λ = 220 nm
n.dm.—not determined or not determinable 6.4 General Synthesis Procedures Method A: Peptide Bond Attachment by the Mixed Anhydride Method Using CFIBE as Activation Reagent 10 mmol of N-terminally protected amino acid or peptide are dissolved in 20 ml of absolute THF. The solution is cooled to −15° C.±2° C. With stirring in each case, 10 mmol of N-MM and 10 mmol of chloroformic acid isobutyl ester are added in succession, the stated temperature range being strictly adhered to. After approximately 6 min, 10 mmol of the amino component is added. When the amino component is a salt, a further 10 mmol of N-MM is then added to the reaction mixture. The reaction mixture is then stirred for 2 h in the cold state and overnight at room temperature.

The reaction mixture is concentrated using a rotary evaporator, taken up in EA, washed with 5% $KH_2SO_4$ solution, saturated $NaHCO_3$ solution and saturated NaCl solution and dried over $NaSO_4$. After removal of the solvent in vacuo, the compound is recrystallized from EA/pentane.

Method B: Peptide Bond Attachment by the Mixed Anhydride Method Using Pivalic Acid Chloride as Activation Reagent 10 mmol of N-terminally protected amino acid or peptide are dissolved in 20 ml of absolute THF. The solution is cooled to 0° C. With stirring in each case, 10 mmol of N-MM and 10 mmol of pivalic acid chloride are added in succession, the stated temperature range being strictly adhered to. After approximately 6 min, the mixture is cooled to −15° C. and, once the lower temperature has been reached, 10 mmol of the amino component is added. When the amino component is a salt, a further 10 mmol of N-MM is then added to the reaction mixture. The reaction mixture is then stirred for 2 h in the cold state and overnight at room temperature.

Further working up is carried out as in Method A.

Method C: Peptide Bond Attachment Using TBTU as Activation Reagent 10 mmol of the N-terminally protected amino acid or peptide and 10 mmol of the C-terminally protected amino component are dissolved in 20 ml of absolute DMF. The solution is cooled to 0° C. With stirring in each case, 10 mmol of DIPEA and 10 mmol of TBTU are added in succession. The reaction mixture is stirred for one hour at 0° C. and then overnight at room temperature. The DMF is completely removed in vacuo and the product is worked up as described in Method A.

Method D: Synthesis of an Active Ester (N-Hydroxysuccinimide Ester)

10 mmol of N-terminally protected amino acid or peptide and 10 mmol of N-hydroxysuccinimide are dissolved in 20 ml of absolute THF. The solution is cooled to 0° C. and 10 mmol of dicyclohexylcarbodiimide are added, with stirring. The reaction mixture is stirred for a further 2 h at 0° C. and then overnight at room temperature. The resulting N,N'-dicyclohexylurea is filtered off and the solvent is removed in vacuo and the remaining product is recrystallized from EA/pentane.

Method E: Amide Bond Attachment Using N-Hydroxysuccinimide Esters 10 mmol of the C-terminally unprotected amino component is introduced into an $NaHCO_3$ solution (20 mmol in 20 ml of water). At room temperature and with stirring, 10 mmol of the N-terminally protected N-hydroxysuccinimide ester dissolved in 10 ml of dioxane are slowly added dropwise. Stirring of the reaction mixture is continued overnight and the solvent is then removed in vacuo.

Further working up is carried out as in Method A.

Method F: Cleavage of the Boc Protecting Group 3 ml of 1.1N HCl/glacial acetic acid (Method F1) or 3 ml of 1.1N HCl/dioxane (Method F2) or 3 ml of 50% TFA in DCM (Method F3) are added to 1 mmol of Boc-protected amino acid pyrrolidide, thiazolidide or peptide. The cleavage at RT is monitored by means of TLC. After the reaction is complete (approximately 2 h), the compound is precipitated in the form of the hydrochloride using absolute diethyl ether and is isolated with suction and dried over $P_4O_{10}$ in vacuo. Using methanol/ether, the product is recrystallized or reprecipitated.

Method G: Hydrolysis 1 mmol of peptide methyl ester is dissolved in 10 ml of acetone and 11 ml of 0.1M NaOH solution and stirred at room temperature. The course of the hydrolysis is monitored by means of TLC. After the reaction is complete, the acetone is removed in vacuo. The remaining aqueous solution is acidified, using concentrated $KH_2SO_4$ solution, until a pH of 2-3 is reached. The product is then extracted several times using EA; the combined ethyl acetate fractions are washed with saturated NaCl solution and dried over $NaSO_4$, and the solvent is removed in vacuo. Crystallization from EA/pentane is carried out.

Example 7

$K_i$-Determination

For $K_i$ determination, dipeptidyl peptidase IV from porcine kidney with a specific activity against glycylprolyl-4-nitroaniline of 37.5 U/mg and an enzyme concentration of 1.41 mg/ml in the stock solution was used.

Assay Mixture:

100 μl test compound in a concentration range of $1*10^{-5}$ M-$1*10^{-8}$ M respectively were admixed with 50 μl glycylprolyl-4-nitroaniline in different concentrations (0.4 mM, 0.2 mM, 0.1 mM, 0.05 mM) and 100 μl HEPES (40 mM, pH7.6; ion strength=0.125). The assay mixture was pre-incubated at 30° C. for 30 min. After pre-incubation, 20 µl DPIV (1:600 diluted) was added and measurement of yellow color development due to 4-nitroaniline release was performed at 30° C. and λ=405 nm for 10 min. using a plate reader (HTS7000 plus, Applied Biosystems, Weiterstadt, Germany).

The $K_i$-values were calculated using Graphit version 4.0.13, 4.0.13 and 4.0.15 (Erithacus Software, Ltd, UK).

7.1 Results—Ki Values of DPIV Inhibition

| Compound | Ki [M] |
|---|---|
| H-Asn-pyrrolidine | $1.20 * 10^{-5}$ |
| H-Asn-thiazolidine | $3.5 * 10^{-6}$ |
| H-Asp-pyrrolidine | $1.4 * 10^{-8}$ |
| H-Asp-thiazolidine | $2.9 * 10^{-6}$ |
| H-Asp(NHOH)-pyrrolidine | $1.3 * 10^{-5}$ |
| H-Asp(NHOH)-thiazolidine | $8.8 * 10^{-6}$ |
| H-Glu-pyrrolidine | $2.2 * 10^{-6}$ |
| H-Glu-thiazolidine | $6.1 * 10^{-7}$ |
| H-Glu(NHOH)-pyrrolidine | $2.8 * 10^{-6}$ |
| H-Glu(NHOH)-thiazolidine | $1.7 * 10^{-6}$ |
| H-His-pyrrolidine | $3.5 * 10^{-6}$ |
| H-His-thiazolidine | $1.8 * 10^{-6}$ |
| H-Pro-pyrrolidine | $4.1 * 10^{-6}$ |
| H-Pro-thiazolidine | $1.2 * 10^{-6}$ |
| H-Ile-azidine | $3.1 * 10^{-6}$ |
| H-Ile-pyrrolidine | $2.1 * 10^{-7}$ |
| H-L-threo-Ile-thiazolidine | $8.0 * 10^{-8}$ |
| H-L-allo-Ile-thiazolidine | $1.9 * 10^{-7}$ |
| D-threo-isoleucyl-thiazolidine-fumarate | no inhibition |
| D-allo-isoleucyl-thiazolidine-fumarate | no inhibition |
| H-L-threo-Ile-thiazolidine-succinate | $5.1 * 10^{-8}$ |
| H-L-threo-Ile-thiazolidine-tartrate | $8.3 * 10^{-8}$ |
| H-L-threo-Ile-thiazolidine-fumarate | $8.3 * 10^{-8}$ |
| H-L-threo-Ile-thiazolidine-hydrochloride | $7.2 * 10^{-8}$ |
| H-L-threo-Ile-thiazolidine-phosphate | $1.3 * 10^{-7}$ |
| H-Val-pyrrolidine | $4.8 * 10^{-7}$ |
| H-Val-thiazolidine | $2.7 * 10^{-7}$ |
| Diprotin A | $3.45 * 10^{-6}$ |
| Diprotin B | $2.24 * 10^{-5}$ |
| Nva-Pro-Ile | $6.17 * 10^{-6}$ |
| Cha-Pro-Ile | $5.99 * 10^{-6}$ |
| Nle-Pro-Ile | $9.60 * 10^{-6}$ |
| Phe-Pro-Ile | $1.47 * 10^{-5}$ |
| Val-Pro-Val | $4.45 * 10^{-6}$ |
| Ile-Pro-Val | $5.25 * 10^{-6}$ |
| Abu-Pro-Ile | $8.75 * 10^{-6}$ |
| Ile-Pro-allo-Ile | $5.22 * 10^{-6}$ |
| Val-Pro-allo-Ile | $9.54 * 10^{-6}$ |
| Tyr-Pro-allo-Ile | $1.82 * 10^{-5}$ |
| AOA-Pro-Ile | $1.26 * 10^{-5}$ |
| t-butyl-Gly-Pro-Ile | $3.10 * 10^{-6}$ |
| Ser(Bzl)-Pro-Ile | $2.16 * 10^{-6}$ |
| Aze-Pro-Ile | $2.05 * 10^{-5}$ |
| t-butyl-Gly-Pro-Val | $3.08 * 10^{-6}$ |
| Gln-Pyrr | $2.26 * 10^{-6}$ |
| Gln-Thia | $1.21 * 10^{-6}$ |
| Val-Pro-t-butyl-Gly | $1.96 * 10^{-5}$ |
| t-butyl-Gly-Pro-Gly | $1.51 * 10^{-5}$ |
| Ile-Pro-t-butyl-Gly | $1.89 * 10^{-5}$ |
| t-butyl-Gly-Pro-IleNH₂ | $5.60 * 10^{-5}$ |
| t-butyl-Gly-Pro-D-Val | $2.65 * 10^{-5}$ |
| t-butyl-Gly-Pro-t-butyl-Gly | $1.41 * 10^{-5}$ |
| Ile-cyclopentyl ketone | $6.29 * 10^{-6}$ |
| t-butyl-Gly-cyclohexyl ketone | $2.73 * 10^{-4}$ |
| Ile-cyclohexyl ketone | $5.68 * 10^{-5}$ |
| Val-cyclopentyl ketone | $1.31 * 10^{-5}$ |
| Val-Pro-methyl ketone | $4.76 * 10^{-8}$ |
| Val-Pro-acyloxy methyl ketone | $1.05 * 10^{-9}$ |
| Val-Pro-benzoyl methyl ketone | $5.36 * 10^{-10}$ |
| Val-Pro-benzothiazol methyl ketone | $3.73 * 10^{-8}$ |
| H-Glu-Thia | $6.2 * 10^{-7}$ |
| H-Gly(NHOH)-Thia | $1.7 * 10^{-6}$ |
| H-Glu(Gly₃)-Thia | $1.92 * 10^{-8}$ |
| H-Glu(Gly₅)-Thia | $9.93 * 10^{-8}$ |
| H-Glu(PEG)-Thia | $3.11 * 10^{-6}$ | t-butyl-Gly is defined as:

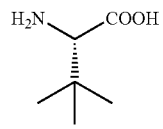

Ser(Bzl) and Ser(P) are defined as benzyl-serine and phosphoryl-serine, respectively. Tyr(P) is defined as phosphoryl-tyrosine.

Example 8

Determination of $IC_{50}$-Values

100 µl inhibitor stock solution were mixed with 100 µl buffer (HEPES pH7.6) and 50 µl substrate (Gly-Pro-pNA, final concentration 0.4 mM) and preincubated at 30° C. Reaction was started by addition of 20 µl purified porcine DPIV. Formation of the product pNA was measured at 405 nm over 10 min using the HTS 7000Plus plate reader (Perkin Elmer) and slopes were calculated. The final inhibitor concentrations ranged between 1 mM and 30 nM. For calculation of IC50 GraFit 4.0.13 (Erithacus Software) was used.

8.1 Results—Determination of $IC_{50}$ Values

| Compound | IC50 [M] |
|---|---|
| Isoleucyl thiazolidine fumarate | $1.28 * 10^{-7}$ |
| Diprotin A | $4.69 * 10^{-6}$ |
| Diprotin B | $5.54 * 10^{-5}$ |
| Phg-Pro-Ile | $1.54 * 10^{-4}$ |
| Nva-Pro-Ile | $2.49 * 10^{-5}$ |
| Cha-Pro-Ile | $2.03 * 10^{-5}$ |
| Nle-Pro-Ile | $2.19 * 10^{-5}$ |
| Ser(P)-Pro-Ile | 0.012 |
| Tyr(P)-Pro-Ile | 0.002 |
| Phe-Pro-Ile | $6.20 * 10^{-5}$ |
| Trp-Pro-Ile | $3.17 * 10^{-4}$ |
| Ser-Pro-Ile | $2.81 * 10^{-4}$ |
| Thr-Pro-Ile | $1.00 * 10^{-4}$ |
| Val-Pro-Val | $1.64 * 10^{-5}$ |
| Ile-Pro-Val | $1.52 * 10^{-5}$ |
| Abu-Pro-Ile | $3.43 * 10^{-5}$ |
| Pip-Pro-Ile | 0.100 |
| Ile-Pro-allo-Ile | $1.54 * 10^{-5}$ |
| Val-Pro-allo-Ile | $1.80 * 10^{-5}$ |
| Tyr-Pro-allo-Ile | $6.41 * 10^{-5}$ |
| AOA-Pro-Ile | $4.21 * 10^{-5}$ |
| t-butyl-Gly-Pro-Ile | $9.34 * 10^{-6}$ |
| Ser(Bzl)-Pro-Ile | $6.78 * 10^{-5}$ |
| Tic-Pro-Ile | 0.001 |
| Orn-Pro-Ile | $2.16 * 10^{-4}$ |
| Gln-Thia | $5.27 * 10^{-4}$ |
| Aze-Pro-Ile | $7.28 * 10^{-5}$ |
| Ile-Hyp-Ile | 0.006 |
| t-butyl-Gly-Pro-Val | $1.38 * 10^{-5}$ |
| Gln-Pyrr | $1.50 * 10^{-5}$ |
| Val-Pro-t-butyl-Gly | $6.75 * 10^{-5}$ |
| t-butyl-Gly-Pro-Gly | $5.63 * 10^{-5}$ |

-continued

| Compound | IC50 [M] |
| --- | --- |
| Ile-Pro-t-butyl-Gly | $8.23 * 10^{-5}$ |
| t-butyl-Gly-Pro-IleNH$_2$ | $2.29 * 10^{-5}$ |
| t-butyl-Gly-Pro-D-Val | $1.12 * 10^{-4}$ |
| t-butyl-Gly-Pro-t-butyl-Gly | $2.45 * 10^{-5}$ |
| Aib-Pro-Ile | no inhibition |
| Ile-cyclopentyl ketone | $3.82 * 10^{-5}$ |
| t-butyl-Gly-cyclohexyl ketone | $2.73 * 10^{-4}$ |
| Ile-cyclohexyl ketone | $2.93 * 10^{-4}$ |
| Val-cyclopentyl ketone | $4.90 * 10^{-5}$ |
| Val-cyclohexyl ketone | 0.001 |
| Val-Pro-methyl ketone | $5.79 * 10^{-7}$ |
| Val-Pro-acyloxy methyl ketone | $1.02 * 10^{-8}$ |
| Val-Pro-benzoyl methyl ketone | $1.79 * 10^{-8}$ |
| Val-Pro-benzothiazol methyl ketone | $1.38 * 10^{-7}$ | t-butyl-Gly is defined as:

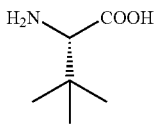

Ser(Bzl) and Ser(P) are defined as benzyl-serine and phosphoryl-serine, respectively. Tyr(P) is defined as phosphoryl-tyrosine.

Example 9

Inhibition of DPIV-Like Enzymes—Dipeptidyl Peptidase II

DP II (3.4.14.2) releases N-terminal dipeptides from oligopeptides if the N-terminus is not protonated (McDonald, J. K., Ellis, S. & Reilly, T. J., 1966, *J. Biol. Chem.*, 241, 1494-1501). Pro and Ala in Pi-position are preferred residues. The enzyme activity is described as DPIV-like activity, but DP II has an acidic pH-optimum. The enzyme used was purified from porcine kidney.

Assay:
100 µl glutaminyl pyrrolidine or glutaminyl thiazolidine in an concentration range of $1*10^{-4}$ M-$5*10^{-8}$ M were admixed with 100 µl µl buffer solution (40 mM HEPES, pH7.6, 0.015% Brij, 1 mM DTT), 50 µl lysylalanylaminomethylcoumarine solution (5 mM) and 20 µl porcine DP II (250fold diluted in buffer solution). Fluorescence measurement was performed at 30° C. and $\lambda_{exiatation}$=380 nm, $\lambda_{emission}$=465 nm for 25 min using a plate reader (HTS7000plus, Applied Biosystems, Weiterstadt, Germany). The $K_i$-values were calculated using Graphit 4.0.15 (Erithacus Software, Ltd., UK) and were determined as $K^i$=$8.52*10^{-5}$ M±$6.33*10^{-6}$ M for glutaminyl pyrrolidine and $K_i$=$1.07*10^{-5}$ M±$3.81*10^{31\ 7}$ M for glutaminyl thiazolidine.

Example 10

Cross Reacting Enzymes

Glutaminyl pyrrolidine and glutaminyl thiazolidine were tested for their cross reacting potency against dipeptidyl peptidase I, prolyl oligopeptidase and prolidase.

Dipeptidyl Peptidase I (DP I, Cathepsin C):
DP I or cathepsin C is a lysosomal cysteine protease which cleaves off dipeptides from the N-terminus of their substrates (Gutman, H. R. & Fruton, J. S., 1948, *J. Biol: Chem.*, 174, 851-858). It is classified as a cysteine protease. The enzyme used was purchased from Qiagen (Qiagen GmbH, Hilden, Germany). In order to get a fully active enzyme, the enzyme was diluted 1000fold in MES buffer pH5.6 (40 mM MES, 4 mM DTT, 4 mM KCl, 2 mM EDTA, 0.015% Brij) and pre-incubated for 30 min at 30° C.

Assay:
50 µl glutaminyl pyrrolidine or glutaminyl thiazolidine in a concentration range of $1*10^{-5}$ M-$1*10^{-7}$ M were admixed with 110 µl buffer-enzyme-mixture. The assay mixture was pre-incubated at 30° C. for 15 min. After pre-incubation, 100 µl histidylseryl-β-nitroaniline ($2*10$-5M) was added and measurement of yellow color development due to β-nitroaniline release was performed at 30° C. and $\lambda_{excitation}$=380 nm, $\lambda_{emission}$=465 nm for 10 min., using a plate reader (HTS7000 plus, Applied Biosystems, Weiterstadt, Germany).

The $IC_{50}$-values were calculated using Graphit 4.0.15 (Erithacus Software, Ltd., UK). No inhibition of the DP I enzyme activity by glutaminyl pyrrolidine or glutaminyl thiazolidine was found.

Prolyl Oligopeptidase (POP)
Prolyl oligopeptidase (EC 3.4.21.26) is a serine type endoprotease which cleaves off peptides at the N-terminal part of the Xaa-Pro bond (Walter, R., Shlank, H., Glass, J. D., Schwartz, I. L. & Kerenyi, T. D., 1971, *Science*, 173, 827-829). Substrates are peptides with a molecular weight up to 3000 Da. The enzyme used was a recombinant human prolyl oligopeptidase. Recombinant expression was performed in *E. coli* under standard conditions as described elsewhere in the state of the art.

Assay:
100 µl glutaminyl pyrrolidine or glutaminyl thiazolidine in an concentration range of $1*10^{-4}$ M-$5*10^{-8}$ M were admixed with 100 µl µl buffer solution (40 mM HEPES, pH7.6, 0.015% Brij, 1 mM DTT) and 20 µl POP solution. The assay mixture was pre-incubated at 30° C. for 15 min. After pre-incubation, 50 µl glycylprolylprolyl-4-nitroaniline solution (0.29 mM) was added and measurement of yellow color development due to 4-nitroaniline release was performed at 30° C. and λ=405 nm for 10 min using a plate reader (sunrise, Tecan, Crailsheim, Germany). The $IC_{50}$-values were calculated using Graphit 4.0.15 (Erithacus Software, Ltd., UK). No inhibition of POP activity by glutaminyl pyrrolidine or glutaminyl thiazolidine was found.

Prolidase (X-Pro Dipeptidase)
Prolidase (EC 3.4.13.9) was first described by Bergmann & Fruton (Bergmann, M. & Fruton, J S, 1937, *J. Biol. Chem.* 189-202). Prolidase releases the N-terminal amino acid from Xaa-Pro dipeptides and has a pH optimum between 6 and 9.

Prolidase from porcine kidney (ICN Biomedicals, Eschwege, Germany) was solved (1 mg/ml) in assay buffer (20 mM NH$_4$(CH$_3$COO)$_2$, 3 mM MnCl$_2$, pH 7.6). In order to get a fully active enzyme the solution was incubated for 60 min at room temperature.

Assay:
450 µl glutaminyl pyrrolidine or glutaminyl thiazolidine in an concentration range of $5*10^{-3}$ M-$5*10^{-7}$ M were admixed with 500 µl buffer solution (20 mM NH$_4$ (CH$_3$COO)$_2$, pH 7.6) and 250 µl Ile-Pro-OH (0.5 mM in the assay mixture). The assay mixture was pre-incubated at 30° C. for 5 min. After pre-incubation, 75 μl Prolidase (1:10 diluted in assay buffer) were added and measurement was performed at 30° C. and λ=220 nm for 20 min using a UV/Vis photometer, UV1 (Thermo Spectronic, Cambridge, UK).

The IC 50-values were calculated using Graphit 4.0.15 (Erithacus Software, Ltd., UK). They were determined as $IC_{50}>3$ mM for glutaminyl thiazolidine and as $IC_{50}=3.4*10^{-4}$ M±5.63*10$^{-5}$ for glutaminyl pyrrolidine.

Example 11

Determination of DPIV Inhibiting Activity After Intravasal and Oral Administration to Wistar Rats Animals Male Wistar rats (Shoe: Wist(Sho)) with a body weight ranging between 250 and 350 g were purchased from Tierzucht Schönwalde (Schönwalde, Germany).

Housing Conditions

Animals were single-caged under conventional conditions with controlled temperature (22±2° C.) on a $^{12}/_{12}$ hours light/dark cycle (light on at 06:00 AM). Standard pelleted chow (ssniff® Soest, Germany) and tap water acidified with HCl were allowed ad libitum.

Catheter Insertion into Carotid Artery

After ≧one week of adaptation at the housing conditions, catheters were implanted into the carotid artery of Wistar rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of catheter dysfunction, a second catheter was inserted into the contra-lateral carotid artery of the respective rat. After one week of recovery from surgery, this animal was reintegrated into the study. In case of dysfunction of the second catheter, the animal was withdrawn from the study. A new animal was recruited and the experiments were continued in the planned sequence, beginning at least 7 days after catheter implantation.

Experimental Design

Rats with intact catheter function were administered placebo (1 ml saline, 0.154 mol/l) or test compound via the oral and the intra-vasal (intra-arterial) route.

After overnight fasting, 100 μl samples of heparinised arterial blood were collected at −30, −5, and 0 min. The test substance was dissolved freshly in 1.0 ml saline (0.154 mol/l) and was administered at 0 min either orally via a feeding tube (75 mm; Fine Science Tools, Heidelberg, Germany) or via the intra-vasal route. In the case of oral administration, an additional volume of 1 ml saline was injected into the arterial catheter. In the case of intra-arterial administration, the catheter was immediately flushed with 30 μl saline and an additional 1 ml of saline was given orally via the feeding tube.

After application of placebo or the test substances, arterial blood samples were taken at 2.5, 5, 7.5, 10, 15, 20, 40, 60 and 120 min from the carotid catheter of the conscious unrestrained rats. All blood samples were collected into ice cooled Eppendorf tubes (Eppendorf-Neteheler-Hinz, Hamburg, Germany) filled with 10 μl 1M sodium citrate buffer (pH 3.0) for plasma DPIV activity measurement. Eppendorf tubes were centrifuged immediately (12000 rpm for 2 min, Hettich Zentrifuge EBA 12, Tuttlingen; Germany): The plasma fractions were stored on ice until analysis or were frozen at −20° C. until analysis. All plasma samples were labelled with the following data:

Code number

Animal Number

Date of sampling

Time of sampling

Analytical Methods

The assay mixture for determination of plasma DPIV activity consisted of 80 μl reagent and 20 μl plasma sample. Kinetic measurement of the formation of the yellow product 4-nitroaniline from the substrate glycylprolyl-4-nitroaniline was performed at 390 nm for 1 min at 30° C. after 2 min pre-incubation at the same temperature. The DPIV activity was expressed in mU/ml.

Statistical Methods

Statistical evaluations and graphics were performed with PRISM® 3.02 (GraphPad Software, Inc.). All parameters were analysed in a descriptive manner including mean and SD.

11.1 Results—In Vivo DPIV-Inhibition at $t_{max}$

| STRUCTURE | Dose (mg/kg) | i.v. (%) | p.o. (%) |
|---|---|---|---|
| Gln-Pyrr | 100 | 80 | 67 |
| Gln-Thia | 100 | 88 | 71 |
| Diprotin A | 100 | 73 | no inhibition |
| Diprotin B | 100 | 50 | no inhibition |
| Tyr(P)-Pro-Ile | 100 | 37 | no inhibition |
| t-butyl-Gly-Pro-Ile | 100 | 71 | 28 |
| t-butyl-Gly-Pro-Val | 100 | 72 | 25 |
| Ala-Val-Pro-acyloxy methyl ketone | 100 | 89 | 86 |
| Ala-Val-Pro-benzoyl-methyl ketone | 100 | 97 | 76 |
| Ile-cyclopentyl ketone | 100 | 34 | 15 |

Example 12

Action of Side Chain-Modified Glutamyl Thiazolidines as Non-Readily-Transportable DPIV-Inhibitors Side chain-modified glutamyl thiazolidines having a structure H-Glu(X)-Thia were synthesised, with polyethylene glycol or glycine oligomers of various chain lengths being used as X (see Method A of example for description of synthesis). The binding characteristics of those derivatives and their transportability by the peptide transporter PepT1 were investigated.

Surprisingly, it was found that the side chain modifications alter the binding characteristics of the compounds to DPIV only to a slight extent. In contrast, the ability of the inhibitors to be transported by the peptide transporter is dramatically diminished by the side chain modification.

Side chain modified inhibitors of DPIV or DPIV-like enzymes are therefore well suited to achieving site directed inhibition of DPIV in the body.

12.1 Results: Transportability of Selected DPIV-Inhibitors.

| Compound amino acid thiazolidines | EC50 (mM)[1] | $I_{max}$ (nA)[2] |
|---|---|---|
| H-Ile-Thia | 0.98 | 25 ± 8 |
| H-Glu-Thia | 1.1 | 35 ± 13 |
| side chain-modified glutamylthiazolidines | | |
| H-Gly(NHOH)-Thia | 3.18 | 42 ± 11 |
| H-Glu(Gly$_3$)-Thia | 8.54 | n.d.[3] |
| H-Glu(Gly$_5$)-Thia | >10 | n.d.[3] |
| H-Glu(PEG)-Thia | >10 | n.d.[3] |

[1]Effective concentrations of the compounds inhibiting the binding of
[3]H-D-Phe-Ala (80 mM) to PepT1-expressing *P. pastoris* cells by 50%
($EC_{50}$ values)
[2]Transport characteristics at PepT1-expressing oocytes of *X. leavis* - by means of two-electrode voltage clamp method, I = inward currents generated by the transport

Example 13

In Vivo Cancer Cell Adhesion Assay

Using a novel in vivo adhesion assay which takes advantage of vital dye labeled tumor cells and their detection in the target tissue in situ (von Hörsten et al, 2000; Shingu et al., 2002), the current example investigates whether the in vivo adhesion of MADB106 tumor cells differs in DPIV in treated wild type F344 rats and F344 substrains with a mutation of the DPIV gene.

Animals, Injection of Tumor Cells and Processing of Lungs

F344USA, F344JAP and F344GER substrains were obtained from a breeding colony at the Central Animal Laboratory at Hannover Medical School, Germany. All substrains were bred for one generation and maintained in a specific-pathogen-free facility at 25° C. under a 12 h light-12 h dark cycle (light on at 07.00 h), with ad libitum access to food and water. The exact number of animals used per experiment is indicated by the F values with at least four animals per condition and time point.

Cell culture, injection of tumor cells, dissection of the animals and immunohistochemistry were conducted as previously described (von Hörsten et al., 2000). In brief, 1×10$^6$ MADB106 tumor cells derived from log phase of tumor growth were injected via the lateral tail vein and lungs removed at different time points thereafter. For in situ quantification of tumor cells at early time points after injection (30 min), cells were vital dye stained using the fluorescein derivate 5- (and -6)-carboxyfluorescein diacetate succinimidyl ester (CFSE) before injection. For quantification of lung surface colonies at later time points (2 weeks after tumor cell inoculation), en-bloc dissected lungs and the heart were injected with 8 ml Bouin's solution (72% saturated picric acid solution, 23% formaldehyde, and 5% glacial acetic acid) and fixed in the same solution until lung surface nodules were counted (see below).

Experiments

Four experiments were conducted:

Effect of a single injection of isoleucyl thiazolidine fumarate (2 mg i.v.+isoleucyl thiazolidine fumarate 2 mg i.p.) on lung tumor colonization in F344USA wild-type rats;

Effect of single injection of isoleucyl thiazolidine fumarate 2 mg i.v.+isoleucyl thiazolidine fumarate 2 mg i.p. on tumor cell adhesion to lungs of F344JAP, F344GER and F344USA rats;

Effect of single injection of isoleucyl cyanopyrrolidine (0.1 mg i.v.+0.1 mg i.p.) on tumor cell adhesion to lungs of F344USA wild-type rats;

Effect of single injection of valyl-pyrrolidine fumarate (0.1 mg i.v.+0.1 mg i.p.) on tumor cell adhesion to lungs of F344USA wild-type rats;

Immunohistochemistry of CFSE-Labeled Tumor Cells in Lungs

Immunostaining of CFSE-labeled MADB106 tumor cells was achieved using mAb characterizing the intracellular CFSE antigen (anti-CFSE; mAb DE1, Boehringer, Mannheim, Germany; mouse, 1:100). For immunohistochemistry, one or two consecutive APAAP stainings were performed as previously described (von Hörsten et al, 2000; Shingu et al., 2002). Control sections were included in which one or both primary antibodies were omitted.

Quantification of Tumor Targets: In Vivo/In Situ Cell Adhesion Assay

Vital dye (Carboxyfluorescein; CFSE) labeling of MADB106 tumor cells allows the quantification of tumor cells and NK cells in thick sections of lung tissue by stereology in situ (von Hörsten et al, 2000). In the present study we produced thin sections (8 µm) of the same lungs (n=10) and performed additional microscopic counting by image analysis of DE1 positive cells. This was done to further simplify the previously validated stereological quantification technique. Therefore, in the present study, the assessment of DE1 positive tumor cells in lung tissue from different substrains 30 min after tumor inoculation was carried out using image analysis approach. All CFSE-labeled MADB106 tumor cells and leukocyte subsets within a grid on the ocular lens were counted (Zeiss Kpl-W 12.5×; grid 0.75×0.75 mm=0.5625 mm$^2$/grid, using a Zeiss Neofluar objective, ×10, NA=0.3). Each right upper lobe of the lungs was sectioned at 6 randomly chosen non-adjacent levels. From each level, three sections were evaluated. On average, 30 grid numbers per section were examined (i.e. 0.5625 mm$^2$/grid×30 grids×3 sections×6 levels) resulting in an area per animal of 3.04 cm$^2$.

Quantification of Macrometastasis on Lungs

For quantification of lung surface colonies at later time points (2 weeks after tumor cell inoculation), en-bloc dissected lungs and the heart were injected with 8 ml Bouin's solution (72% saturated picric acid solution, 23% formaldehyde, and 5% glacial acetic acid) and fixed in the same solution until lung surface nodules were counted. Three areas per lungs were examined using a gauge (1 cm$^2$) and lung surface colony numbers were expressed as mean/cm$^2$ according to the method of Wexler (Wexler, 1966).

Statistical Analysis

Data from in vivo adhesion assay were analyzed by one-way ANOVAs and Fisher's PLSD post hoc tests, if appropriate. An asterisk indicates significant post hoc effects vs. saline (SHAM) treated controls obtained by Fisher's PLSD. All data are presented as means±S.E.M.

Results

Effect of a Single Injection of Isoleucyl Thiazolidine Fumarate on Lung Tumor Colonization in F344USA Rats The number of lung surface tumor colonies after single isoleucyl thiazolidine fumarate administration in F344 rats 2 weeks after injection of MADB106 tumor cells is illustrated in FIG. 1. One factor ANOVA revealed no significant effect (F(1,12)=3.2; p=0.1 n.s.) on colony numbers. A trend toward decreased colony numbers in experimental rats was evident.

Figure 2:
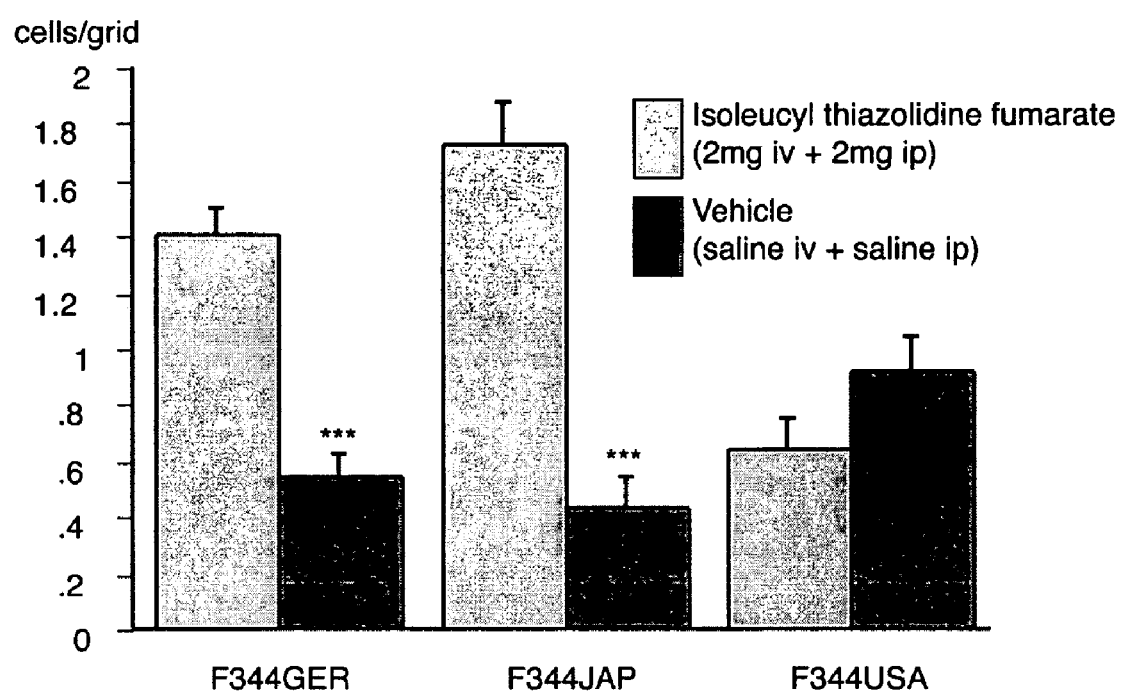
FIG. 2: Effect of single injection of isoleucyl thiazolidine fumarate on tumor cell adhesion 30 min after injection in F344 substrains mutant for DPIV. CFSE labeled MADB106 tumor cells were injected via the lateral tail vein and lungs were collected 30 min after inoculation. Note the promoting effect in mutant F344GER and F344JAP rats in contrast to the lack of effects in wild-type F344 rats. Data represent means±SEM; *$p<0.05$ reflecting significant differences vs. wild-type F344USA animals determined by ANOVA and Fisher PLSD.

Effect of Single Injection of Isoleucyl Thiazolidine Fumarate on Tumor Adhesion in F344JAP, F344GER and F344USA Rats The mean number of CFSE positive cells in lung tissue at 30 min after inoculation of MADB106 tumor cells in the three substrains is illustrated in FIG. 2. Two-way ANOVA showed a significant effect of "substrain" ($F(2,43)=3.5$; $p<0.04$) and "treatment" ($F(1,43)=44.1$; $p<0.0001$), as well as a significant interaction factors but no significant interaction ($F(2,43)=26.2$; $p<0.0001$). Separate one factor ANOVAs split for these substrains revealed that these effects are significant.

Figure 3:
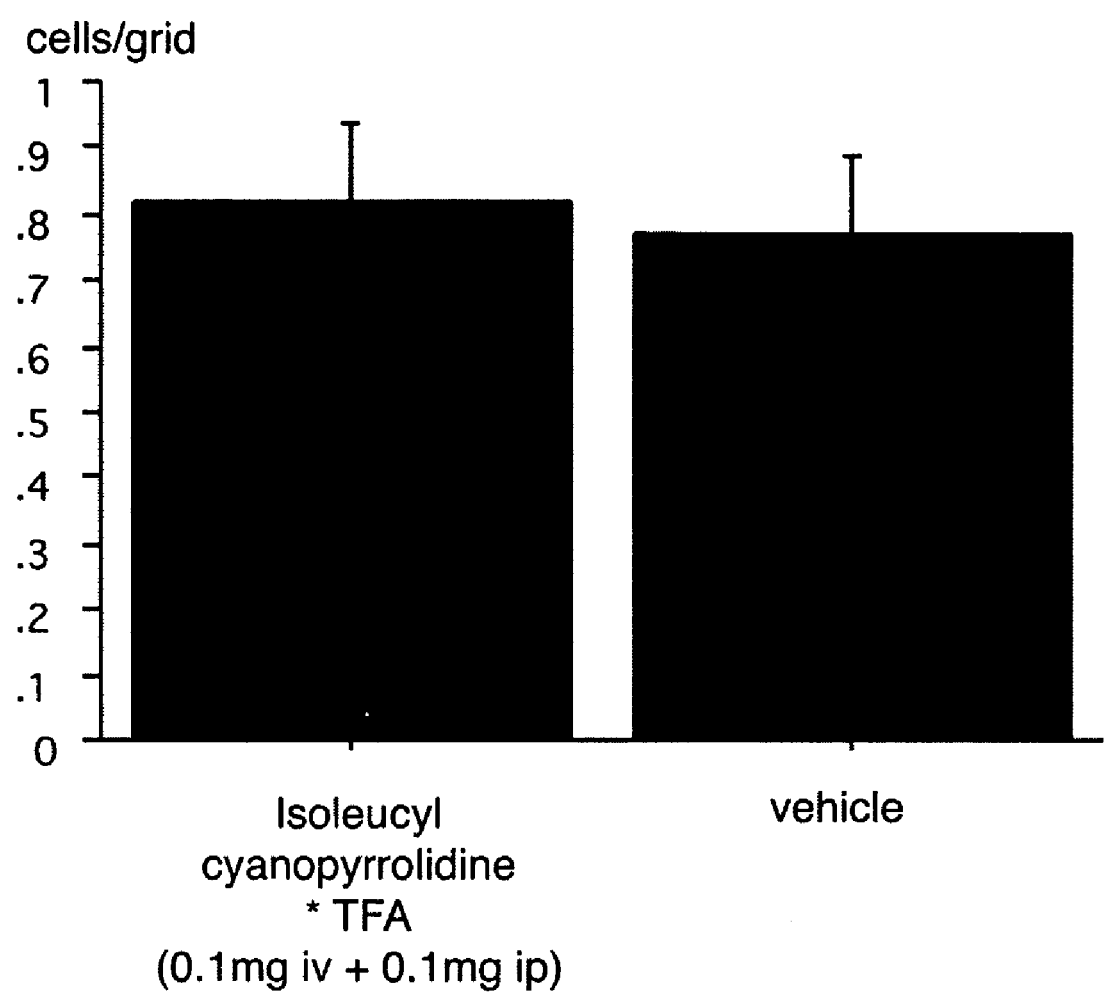
FIG. 3: Effect of single injection of isoleucyl cyanopyrrolidine TFA on tumor cell adhesion 30 min after injection in F344USA rats. CFSE labeled MADB106 cancer cells were injected via the lateral tail vein and lungs were collected 30 min after inoculation. CFSE positive tumor cells in lungs were quantified by means of immunohistology and image analysis. Data represent means±SEM; significant differences vs. saline treated controls were not found.

Effect of Single Injection of Isoleucyl Cyanopyrrolidine TFA on Tumor Adhesion of F344USA Rats The mean number of CFSE positive cells in lung tissue at 30 min after inoculation of MADB106 tumor cells after isoleucyl cyanopyrrolidine TFA treatment is illustrated in FIG. 3. ANOVA showed no significant effect of "treatment" ($F(1,18)=0.1$; $p=0.8$ n.s.).

Figure 4:
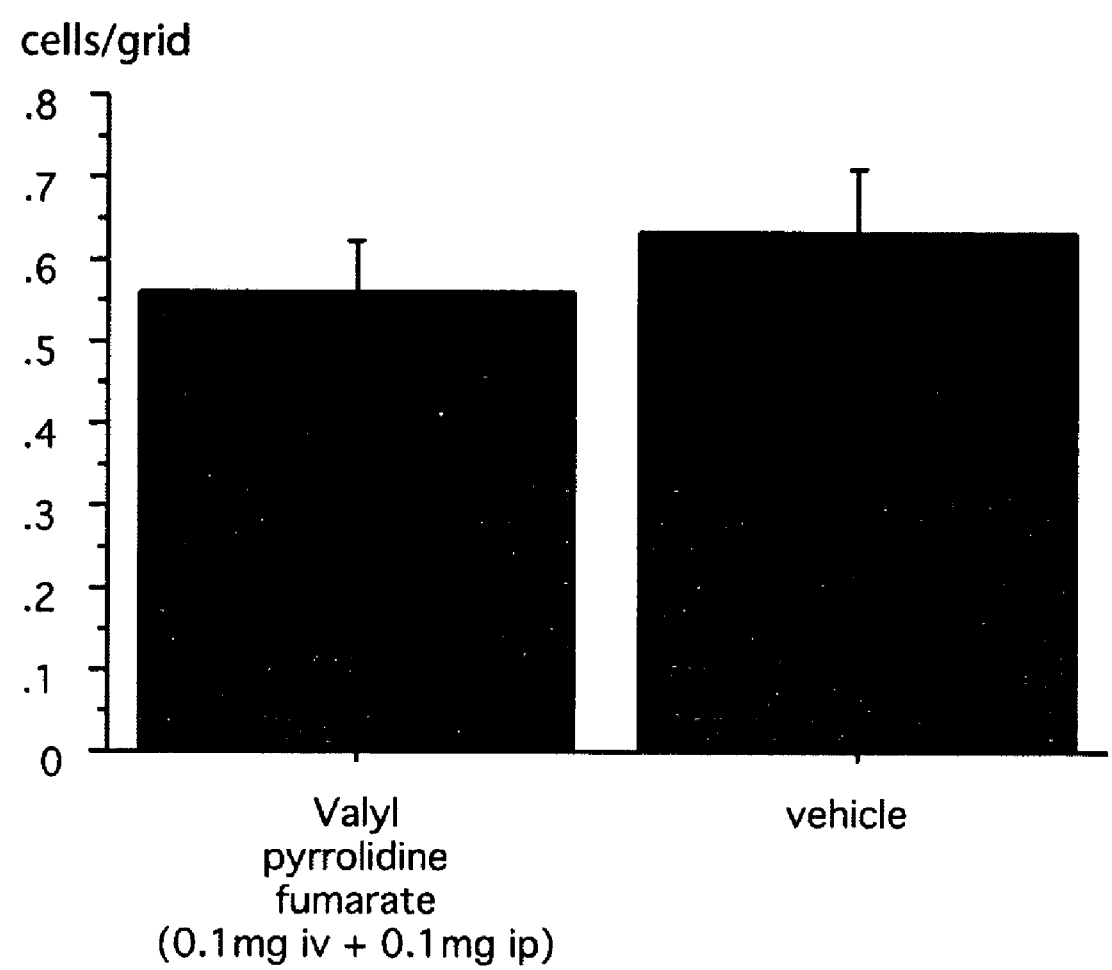
FIG. 4: Effect of single injection of valyl pyrrolidine fumarate on tumor cell adhesion 30 min after injection in F344USA rats. CFSE labeled of MADB106 adenocarcinoma cells were injected via the lateral tail vein and lungs were collected 30 min after inoculation. CFSE positive tumor cells in lungs were quantified by means of immunohistology and image analysis. Data represent means±SEM; significant differences vs. saline treated controls were not found.

Effect of Single Injection of Valyl Pyrrolidine Fumarate on Tumor Adhesion of F344USA Rats The mean number of CFSE positive cells in lung tissue at 30 min after inoculation of MADB106 tumor cells after valyl pyrrolidine fumarate treatment is illustrated in FIG. 4. ANOVA showed no significant effect of "treatment" ($F(1,18)=0.6$; $p=0.5$ n.s.).

Discussion

Tumor cell adhesion and colonization is significantly modified by single injection of isoleucyl thiazolidine fumarate only in mutant F344 substrains suggesting an interaction of the ligand with mutant DPIV and tumor cells. Since the ligand did not significantly affect tumor adhesion in wild type F344USA rats, this may indicate that compound is not interacting with the binding site of MADB106 tumor cells.

Example 14

Cancer Colonization Assays

In the previous example it was demonstrated that MADB106 tumor cell adhesion is significantly modified by a single administration of isoleucyl thiazolidine fumarate only in mutant F344 substrains but not in wild type DPIV expressing F344USA rats. DPIV inhibitors/ligands may interact with the growth of tumor metastases exhibiting properties similar to chemotherapeutic compounds and/or immunotherapeutical compounds. In contrats to that, the current example investigates whether the tumor colonization of MADB106 tumor cells differs in chronically DPIV-inhibitor treated wild type F344 rats.

Animals, Injection of Tumor Cells and Processing of Lungs

F344USA rats were obtained from a breeding colony at the Central Animal Laboratory at Hannover Medical School, Germany. All rats were bred at least for one generation and maintained in a specific-pathogen-free facility at 25° C. under a 12 h light-12 h dark cycle (light on at 07.00 h), with ad libitum access to food and water. The exact number of animals used per experiment is indicated by the F values with at least four animals per condition and time point.

Cell culture, injection of tumor cells, dissection of the animals and immunohistochemistry were conducted as previously described (von Hörsten et al., 2000; Shingu et al., 2002). In brief, $1\times10^6$ MADB106 tumor cells derived from log phase of tumor growth were injected via the lateral tail vein and lungs removed at different time points thereafter. For in situ quantification of tumor cells at early time points after injection (30 min), cells were vital dye stained using the fluorescein derivate 5- (and -6)-carboxyfluorescein diacetate succinimidyl ester (CFSE) before injection. For quantification of lung surface colonies at later time points (2 weeks after tumor cell inoculation), en-bloc dissected lungs and the heart were injected with 8 ml Bouin's solution (72% saturated picric acid solution, 23% formaldehyde, and 5% glacial acetic acid) and fixed in the same solution until lung surface nodules were counted (see below).

Experiments

Two experiments were conducted:
Effect of chronic infusion of different dosages of isoleucyl thiazolidine fumarate (0 mg, 0.04 mg, 0.4 mg, 4 mg/24 h intragastral via implanted osmotic minipumps) on body weight change and lung tumor colonization in F344USA wild-type rats Effect of chronic infusion of isoleucyl thiazolidine fumarate (4 mg/24 h intragastral via implanted osmotic minipumps), lisoleucyl cyanopyrrolidine TFA (0.1 mg/24 h intragastral via implanted osmotic minipumps) and valyl pyrrolidine fumarate (0.1 mg/24 h intragastral via implanted osmotic minipumps) on lung tumor colonization in F344USA wild-type rats.

Implantation of Osmotic Minipumps for Chronic Intragastric Infusion of Compounds Osmotic minipumps (Alzet model 2ML4; flow rate, 2.5 µl/hr; Alza Corporation), administering a constant supply of the different compounds, aseptically prefilled with either saline or DPIV inhibitor were placed subcutaneously in the abdominal area. Minipums were attached to a cannula via polyethylene tubing. The cannula was implanted intragastrically with a heating-induced enlarged tip of the cannula in the lumen of the gaster.

Quantification of Macrometastasis on Lungs

For quantification of lung surface colonies at later time points (2 weeks after tumor cell inoculation), en-bloc dissected lungs and the heart were injected with 8 ml Bouin's solution (72% saturated picric acid solution, 23% formaldehyde, and 5% glacial acetic acid) and fixed in the same solution until lung surface nodules were counted. Three areas per lungs were examined using a gauge (1 $cm^2$) and lung surface colony numbers were expressed as mean/$cm^2$ according to the method of Wexler (Wexler, 1966).

Statistical Analysis

Data from in vivo body weight gain and number of lung surface tumor colonies were analyzed by one-way ANOVAs and Fisher's PLSD post hoc tests, if appropriate. An asterisk indicates significant post hoc effects vs. saline (SHAM) treated controls obtained by Fisher's PLSD. All data are presented as means±S.E.M.

Results

Figure 5:
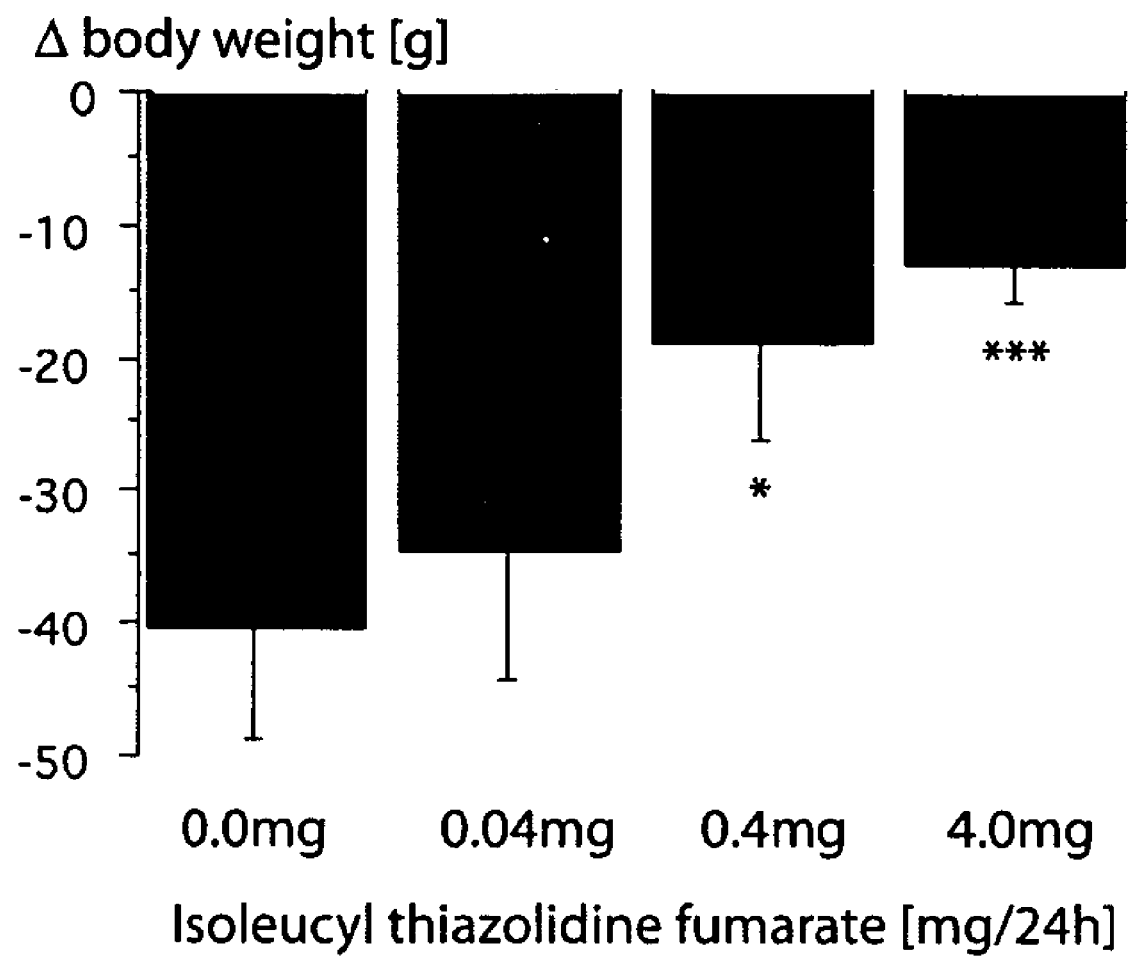
FIG. 5: Effect of chronic intragastric infusion of isoleucyl thiazolidine fumarate on body weight change in grams in F344 rats with lung metastasis. A dose dependent reduction of the loss of body weight after chronic infusion of different dosages of isoleucyl thiazolidine fumarate in F344 rats 2 weeks after injection of MADB106 tumor cells is illustrated. One factor ANOVA revealed a significant effect on body weight, which became significant in the post-hoc analysis at the 0.4 mg and 4 mg dosages. Data represent means±SEM; *$p<0.05$ reflecting significant differences vs. saline treated SHAM controls determined by Fisher PLSD.

Effect of Chronic Infusion of Isoleucyl Thiazolidine Fumarate (0 mg, 0.04 mg, 0.4 mg, 4 mg/24 h) on Lung Tumor Colonization The change of body weight after chronic infusion of different dosages of isoleucyl thiazolidine fumarate in F344 rats 2 weeks after injection of MADB106 tumor cells is illustrated in FIG. 5. One factor ANOVA revealed a significant effect ($F(3,22)=3.5$; $p=0.03$) on body weight, which became significant in the post-hoc analysis at the 0.4 mg and 4 mg dosages.

Figure 6:
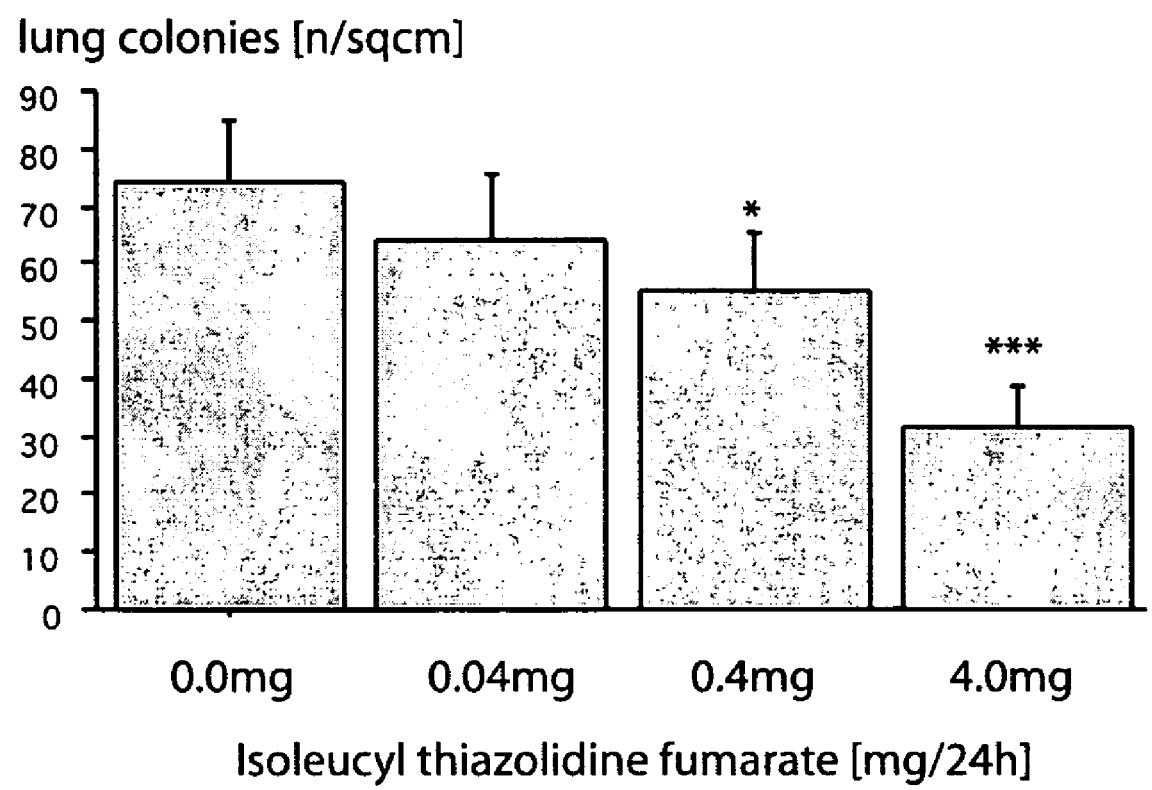
FIG. 6: Effect of chronic intragastric infusion of isoleucyl thiazolidine fumarate on the number of lung tumor colonies in F344 rats. A dose dependent reduction of lung colony numbers after chronic infusion of different dosages of isoleucyl thiazolidine fumarate in F344 rats 2 weeks after injection of MADB106 tumor cells is illustrated. One factor ANOVA revealed a significant effect, which became significant in the post-hoc analysis at the 4 mg dosage. Data represent means±SEM; *$p<0.05$ reflecting significant differences vs. saline treated SHAM controls determined by Fisher PLSD.

The number of lung surface tumor colonies after chronic infusion of different dosages of isoleucyl thiazolidine fumarate in F344 rats 2 weeks after injection of MADB106 tumor cells is illustrated in FIG. 6. One factor ANOVA revealed a significant effect (F(3,22)=3.8; p=0.03) on colony numbers, which became significant in the post-hoc analysis at the 4 mg dosage.

Figure 7:
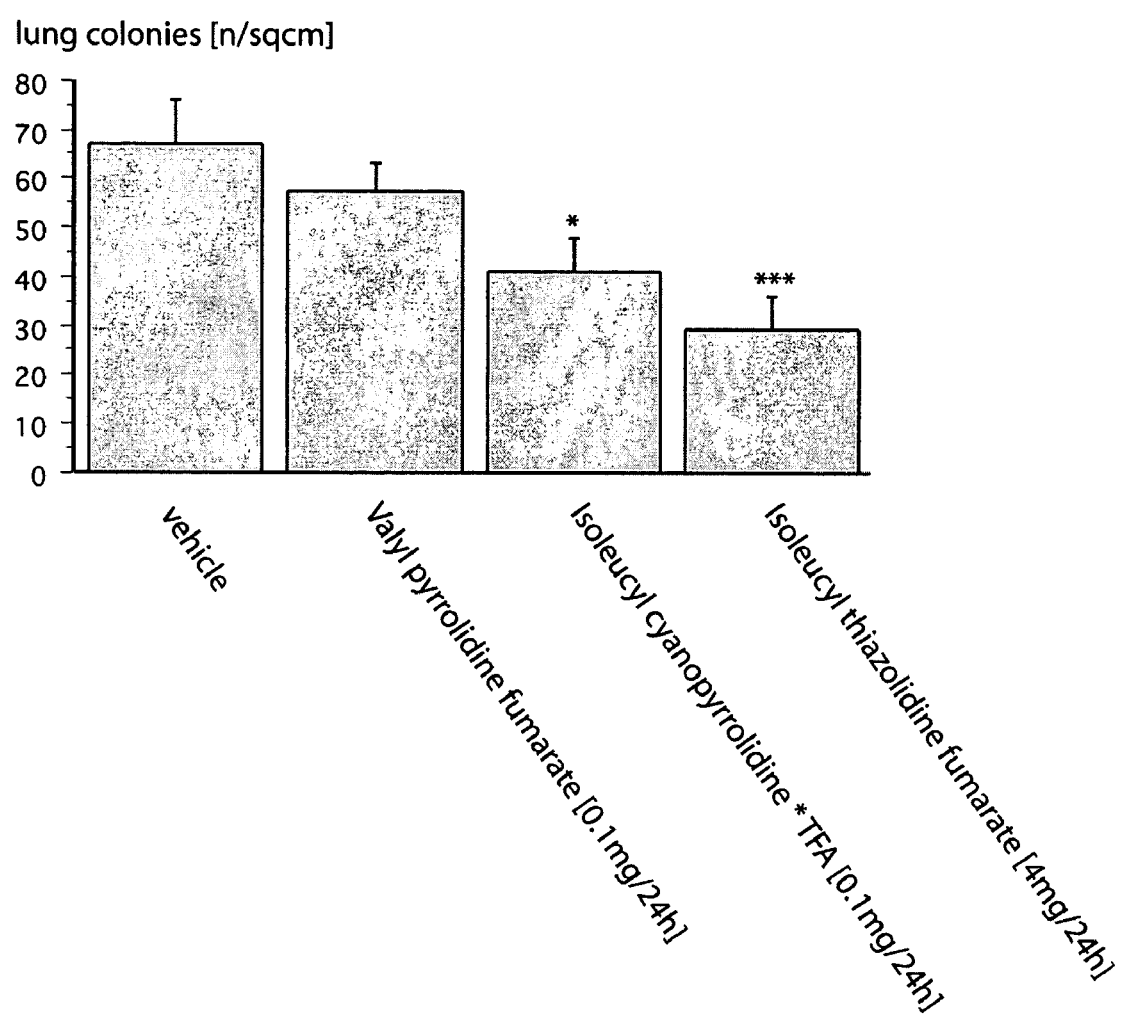
FIG. 7: Effect of chronic intragastric infusion of isoleucyl thiazolidine fumarate; isoleucyl cyanopyrrolidine TFA, and valyl pyrrolidine fumarate on the number of lung tumor colonies in F344 rats. A significant reduction of lung colony numbers after chronic infusion of isoleucyl thiazolidine fumarate and isoleucyl cyanopyrrolidine TFA in F344 rats 2 weeks after injection of MADB106 tumor cells is illustrated. Data represent means±SEM; *$p<0.05$ reflecting significant differences vs. saline treated SHAM controls determined by ANOVA and Fisher PLSD.

Effect of Chronic Infusion of Isoleucyl Thiazolidine Fumarate, Isoleucyl Cyanopyrrolidine TFA, and Valyl Pyrrolidine Fumarate on Lung Tumor Colonization The number of lung surface tumor colonies after chronic infusion of isoleucyl thiazolidine fumarate; isoleucyl cyanopyrrolidine TFA, and valyl pyrrolidine fumarate in F344 rats 2 weeks after injection of MADB106 tumor cells is illustrated in FIG. 7. One factor ANOVA revealed a significant effect (F(3,20)=3.8; p=0.03) on colony numbers, which became significant in the post-hoc analysis for isoleucyl cyanopyrrolidine TFA and isoleucyl thiazolidine fumarate compounds.

Discussion

Metastasis of MADB106 is reduced by chronic treatment using different DPIV Inhibitors (isoleucyl thiazolidine fumarate; isoleucyl cyanopyrrolidine TFA) suggesting protective-like class effects. Possibly, isoleucyl thiazolidine fumarate and isoleucyl cyanopyrrolidine TFA protect from metastasis either via interaction with cell adhesion processes or via a modification of the cellular host defense mechanisms. It is also possible that DPIV inhibitor treatment exhibits cytostatic effects. These antimetastic effects substantiate the biological properties of DPIV Inhibitors for the treatment of cancer and metastatic disease.

REFERENCES

Abdel-Ghany M, Cheng H, Levine R, Pauli B U (1998) Truncated dipeptidyl peptidase IV is a potent antiadhesion and anti-metastasis peptide for rat breast cancer calls. Invasion Metastasis 18: 35-43

Aguirre K M, McCormik R J, Schwarzbauer J E (1994) Fibronectin self-association is mediated by complementary sites within the amino-terminal one-third of the molecule. J Biol Chem 269: 27863-27868

Barlozzari T, Leonhardt J, Wiltrout R H, Herberman R B, Reynolds C W (1985) Direct evidence for the role of LGL in the inhibition of experimental tumor metastases. J Immunol 134: 2783-2789

Bühling F, Kunz D, Reinhold D, Ulmer, A J, Ernst M, Flad H D, Ansorge S (1994) Expression and functional role of dipeptidyl peptidase IV (CD26) on human natural killer cells. Nat Immun 13: 270-279

Cheng H C, Abdel-Ghany M, Elble R C, Pauli B U (1998) Lung endothelial dipeptidyl peptidase IV promotes adhesion and metastasis of rat breast cancer cells via tumor cell surface-associated fibronectin. J Biol Chem 273: 24207-24215

Cheng H C, Abdel-Ghany M, Zhang S, Pauli B U (1999) Is the Fischer 344/CRJ rat a protein-knock-out model for dipeptidyl peptidase IV-mediated lung metastasis of breast cancer?. Clin Exp Metastasis 17: 609-615

Chernousov M A, Fogerty F J, Koteliansky V E, Mosher D F (1991) Role of the I-9 and III-1 modules of fibronectin in formation of an extracellular fibronectin matrix. J Biol Chem 266:10851-10858

De Meester I, Korom S, Van Damme J, Scharpé S (1999) CD26, let it cut or cut it down. Immun today 20: 367-375

Held-Feindt J, Krisch B, Mentlein R (1999) Molecular analysis of the somatostatin receptor subtype 2 in human glioma cells. Mol Brain Res 64: 101-107

Hocking D C, Smith R K, McKeown-Longo P J (1996) A novel role for the integrin-binding III-10 module in fibronectin matrix assembly. J Cell Biol 133: 431-444

Hoshimoto K, Ohta N, Ohkura T, Inaba N (2000) Changes in plasma soluble CD26 and CD30 during pregnancy: markers of Th1/Th2 balance? Gynecol Obstet Inves 50: 260-263

Ingham K C, Brew S A, Huff S, Litvinovich S V (1997) Cryptic self-association sites in type III modules of fibronectin. J Biol Chem 272: 1718-1724

Iwata S, Yamaguchi N, Munakata Y, Ikushima H, Lee J F, Hosono O, Schlossman S F, Morimoto C (1999) CD26/dipeptidyl peptidase IV differentially regulates the chemotaxis of T cells and monocytes toward RANTES: possible mechanism for the switch from innate to acquired immune response. Int Immunol 11: 417-426

Jacobs R, Stoll M, Stratmann G, Leo R, Link H, Schmidt R E (1992) CD16– CD56+natural killer cells after bone marrow transplantation. Blood 79: 3239-3244

Kähne T, Lendeckel U, Wrenger S, Neubert K, Ansorge S, Reinhold D (1999) Dipeptidyl peptidase IV: a cell surface peptidase involved in regulating T cell grwoth (review). Int J Mol Med 4: 3-15

Korom S, De Meester I, Stadlbauer T H, Chandraker A, Schaub M, Sayegh M H, Belyaev A, Haemers A, Scharpe S, Kupiec-Weglinski J W (1997) Inhibition of CD26/dipeptidyl peptidase IV activity in vivo prolongs cardic allograft survival in rat recipients. Transplntation 63: 1495-1500

Mentlein R and Struckhoff G (1989) Purification of two dipeptidylaminopeptidases II from rat brain and their action on proline-containing neuropeptides. J Neurochem 52:1284-1293

Mentlein R (1999) Dipeptidyl-peptidase IV (CD26)—role in the inactivation of regulatory peptides. Regul Pept 85: 9-24

Morla A and Ruoslahti E (1992) A fibronectin self-assembly site involved in fibronectin matrix assembly: reconstruction in a synthetic peptide. J Cell Biol 118: 421-429

Struyf S, Proost P, Schols D, De Clercq E, Opdenakker G, Lenaerts J P, Detheux M, Parmentier M, De Meester I, Scharpe S, Van Damme J (1999) CD26/dipeptidyl-peptidase IV down-regulates the eosinophil chemotactic potency, but not the anti-HIV activity of human eotaxin by affecting its interaction with CC chemokine receptor 3. J Immunol 162: 4903-4909

Tayebati S K, Bronzetti E, Morra di Cella S, Mulatero P, Ricci A, Rossodivita I, Schena M, Schiavone D, Veglio F, Amenta F (2000) In situ hybridization and immunohistochemistry of $\alpha_1$-adrenoceptors in human periperal blood lymphocytes. J Auton Pharmacol 20: 305-312

Thompson N L, Hixson D C, Callanan H, Panzica M, Flanagan D, Faris R A, Hong W J, Hartel-Schenk S, Doyle D (1991) A Fischer rat substrain deficient in dipeptidyl peptidase IV activity makes normal steady-state RNA levels and an altered protein. Use as a liver-cell transplantation model. Biochem J 273: 497-502

Tsuji E, Misumi Y, Fujiwara T, Takami N, Ogata S, Ikehara Y (1992) An active-site mutation ($Gly^{633}$-->Arg) of dipeptidyl peptidase IV causes its retention and rapid degradation in the endoplasmic reticulum. Biochemistry 31: 11921-11927 von Hörsten S, Ballof J, Helfritz F, Nave H, Meyer D, Schmidt R E, Stalp M, Klemm A, Tschernig T, Pabst R (1998) Modulation of innate immune functions by intracerebroventricularly applied neuropeptide Y: dose and time dependent effects. Life Sci 63: 909-922

Wexler H (1966) Accurate identification of experimental pulmonary metastases. J Natl Cancer Inst 36: 641-645.

We claim:

1. A method for treating breast cancer, the method comprising administering to a subject in need thereof a therapeutically effective amount of at least one inhibitor of fibroblast activation protein alpha (FAPα), wherein said inhibitor is an amino acid linked to a thiazolidine or a pyrrolidine group by a peptide bond.

2. The method according to claim 1, wherein treating comprises treating tumor cell metastasis.

3. The method according to claim 1, wherein treating comprises treating tumor colonization.

4. The method according to claim 1 wherein the at least one inhibitor is selected from the group consisting of L-threo-isoleucyl pyrrolidine, L-allo-isoleucyl thiazolidine, L-allo-isoleucyl pyrrolydine, L-glutaminyl thiazolidine, L-glutaminyl pyrrolidine, L-glutamic acid thiazolidine, L-glutamic acid pyrrolidine and salts thereof.

5. A method according to claim 1 wherein the amino acid is selected from the group consisting of leucine, valine, glutamine, glutamic acid, proline, isoleucine, asparagines and asparatic acid.

6. A method for treating breast cancer, the method comprising administering to a subject in need thereof a therapeutically effective amount of a pharmaceutical composition which comprises at least one inhibitor of dipeptidyl peptidase IV (DPIV) or fibroblast activation protein alpha (FAPα), wherein said inhibitor is an amino acid linked to a thiazolidine or a pyrrolidine group by a peptide bond.

7. The method according to claim 6, wherein treating comprises treating tumor cell metastasis.

8. The method according to claim 6, wherein treating comprises treating tumor colonization.

9. The method according to claim 6 wherein the at least one inhibitor is selected from the group consisting of L-threo-isoleucyl pyrrolidine, L-allo-isoleucyl thiazolidine, L-allo-isoleucyl pyrrolydine, L-glutaminyl thiazolidine, L-glutaminyl pyrrolidine, L-glutamic acid thiazolidine, L-glutamic acid pyrrolidine and salts thereof.

10. A method according to claim 6 wherein the amino acid is selected from the group consisting of leucine, valine, glutamine, glutamic acid, proline, isoleucine, asparagines and asparatic acid.

* * * * *